Figure 1:
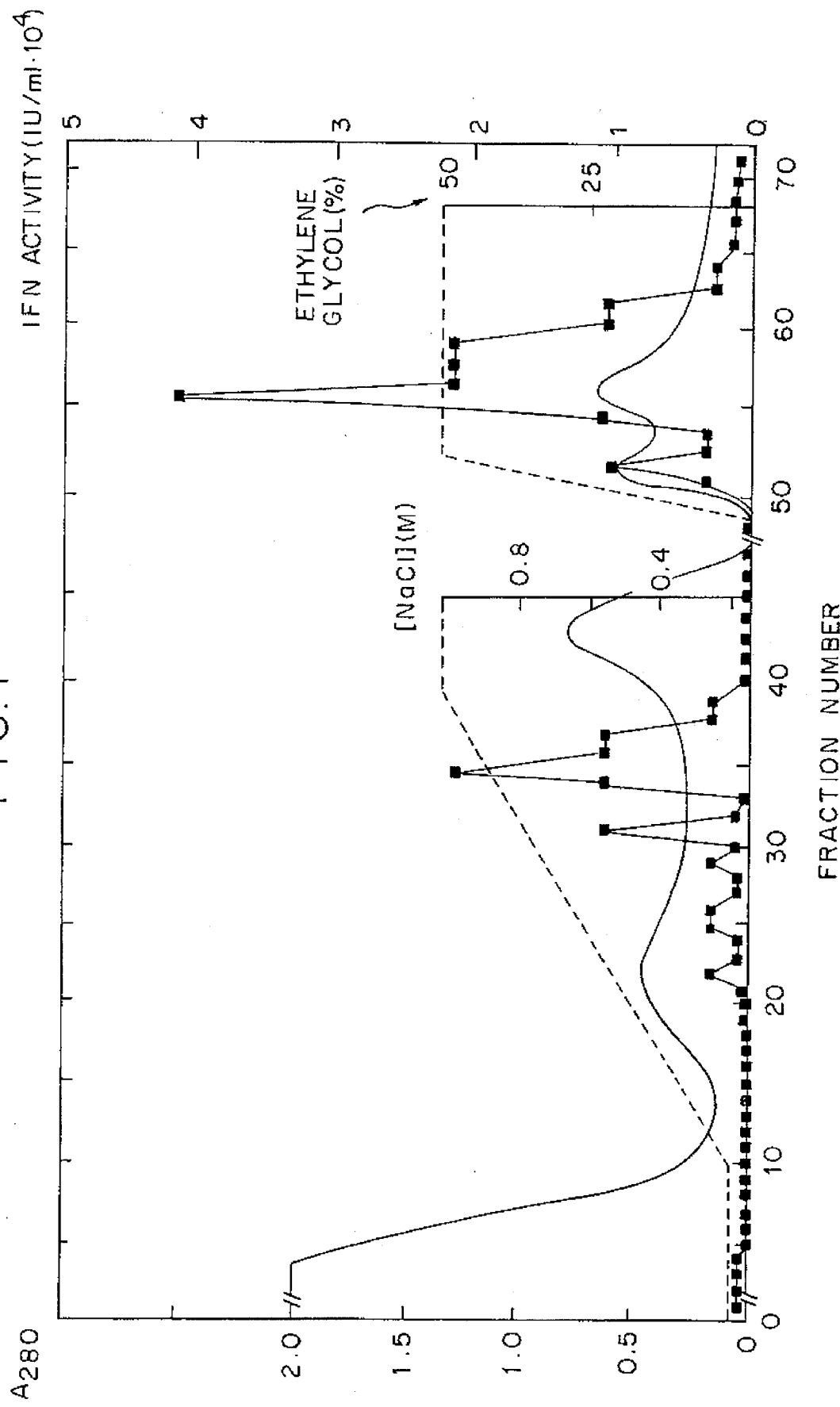

United States Patent [19]

Ebbesen et al.

[11] Patent Number: 5,540,923
[45] Date of Patent: Jul. 30, 1996

[54] INTERFERON PROTEINS

[75] Inventors: Peter Ebbesen, Hojberg; George Aboagye-Mathiesen, Ostbirk; Ferenc D. Toth, Debrecen, all of Denmark

[73] Assignee: Landsforeningen til Kraeftens Bekaemplse, Kobenhavn, Denmark

[21] Appl. No.: 801,816

[22] Filed: Dec. 6, 1991

[51] Int. Cl.$^6$ .............................. C12N 15/00; C12P 21/02; C12Q 1/68; A01N 1/07
[52] U.S. Cl. .................. 424/85.5; 424/85.4; 424/85.6; 530/351
[58] Field of Search .......................... 530/351; 424/85.4, 424/85.6, 85.5

[56] References Cited

U.S. PATENT DOCUMENTS 4,992,271 2/1991 Fernandez et al. ...................... 530/351

FOREIGN PATENT DOCUMENTS 9009806 9/1990 WIPO.

OTHER PUBLICATIONS

G. Aboagye–Mathiesen et al., Characterization of Sendai Virus–Induced Human Placental Trophoblast Interferons Journal of General Virology, 72, pp. 1–5, (1991).

T. Y. Basham et al., Recombinant Interferon–γ Increases HLA–DR Synthesis and Expression, The Journal of Immunology, 130:4, pp. 1492–1494, (1983).

B. H. Butterworth et al., Human Cytotrophoblast Populations Studied by Monoclonal Antibodies Using Single and Double Biotin–Avidin–Peroxidase Immunocytochemistry, The Journal of Histochemistry and Cytochemistry, 33:10, pp. 977–983, (1985).

W. L. Farrar et al., Interleukin—2 Stimulates Association of Protein Kinase C with Plasma Membrane, Nature, 315, pp. 233–235.

W. P. Faulk et al., Human Placentae: View From an Immunological Bias, American Journal of Reproductive Immunology, 21, pp. 108–113.

W. P. Faulk et al., Distribution of $\beta_2$ Microglobulin and HLA in Chorionic Villi of Human Placentae, Nature, 626, pp. 799–802.

M. A. Feinman et al., HLA Antigen Expression and Induction by γ–Interferon in Cultured Human Trophoblasts, American Journal of Obstetrics and Gynecology, 157:6, pp. 1429–1434.

D. C. Flyer et al., Retrovirus–Induced Changes in Major Histocompatibility Complex Antigen Expression Influence Susceptibility to Lysis by Cytotoxic T Lymphocytes, The Journal of Immunology, 135:4, pp. 2287–2292.

N. Harboe et al., Immunization, Isolation of Immunoglobulins, Estimation of Antibody Titre, Scandinavian Journal of Immunology, 2 (Supp 1), pp. 161–164.

J. S. Hunt et al., Interferon—Induces Class I HLA and $\beta_2$–Microglobulin Expression by Human Amnion Cells, The Journal of Immunology, 136:2, pp. 364–367.

H. M. Johnson et al., Vasopressin Replacement of Interleukin 2 Requirement in Gamma Interferon Production: Lymphokine Activity of a Neuroendocrine Hormone, The Journal of Immunology, 129:3, pp. 983–986.

H. M. Johnson et al., Cyclic GMP as the Second Messenger in Helper Cell Requirement for γ–Interferon Production, The Journal of Immunology, 129:6, pp. 2570–2572.

H. M. Johnson et al., Leukotrienes: Positive Signals for Regulation of γ–Interferon Production, The Journal of Immunology, 132:1, pp. 413–416.

M. Kato et al., Expression of HLA Class I and $\beta_2$–Microglobulin on Human Choriocarcinoma Cell Lines: Induction of HLA Class I by Interferon–γ, Placenta, 12, pp. 217–226.

C. Kohler et al., Continuous Cultures of Fused Cells Secreting Antibody of Predefined Specificity, Nature, 256, pp. 495–497.

L. A. Matis et al., Magnitude of Response of Histocompatibility–Restricted T–Cell Clones is a Funciton of the Product of the Concentrations of Antigen and Ia Molecules, Proceeding of National Academy of Science, USA, 80, pp. 6019–6023.

R. Mattsson et al., Placental HMC Claa I Antigen Expression is Induced in Mice Following in Vivo Treatment with Recombinant Interferon–Gamma, Journal of Reproductive Immunology, 19, pp. 115–129.

V. Papermaster et al., Evidence for Suppressor T–Cell Regulation of Human Gamma Interferon Production, Cellular Immunology, 79, pp. 279–287.

L. Paulesu et al., Immunocytochemical Localization of Interferons in Human Trophoblast Populations, Journal of Biological Regulators and Homeostatic Agents, 5:3, pp. 81–85.

C. W. G. Redman et al., Class 1 Major Histocompatibility Complex Antigens on Human Extra–Villous Trophoblast, Immunology, 52, pp. 457–468.

P. S. Steeg et al., Regulation of Murine Macrophage Ia Antigen Expression by a Lymphokine with Immune Interferon Activity, Journal of Experimental Medicine, 156, pp. 1780–1793.

B. A. Torres et al., Interleukin 2 Regulates Immune Interferon (IFNγ) Production by Normal and Suppressor Cell Cultures, The Journal of Immunology, 128:5, pp. 2217–2219.

F. D. Toth et al., Human Trophoblast Interferon: Pattern of Response to Priming and Superinduction of Purified Term Trophoblast and Choriocarcinoma Cells, Journal of Reproductive Immunology, 19, pp. 55–67.

(List continued on next page.)

Primary Examiner—Christina Y. Chan
Assistant Examiner—Lynn Touzeau
Attorney, Agent, or Firm—Iver P. Cooper

[57] ABSTRACT

The invention relates to a method for producing isolating and purifying trophoblast interferon proteins such as β-interferons, $\alpha_I$-interferon proteins, $\alpha_{II}$-interferon proteins, and γ-interferon proteins, and to a method of using the interferon proteins, e.g. for inhibiting tumoral growth or metastatic processes, for preventing graft-versus-host reaction, against leukemia, against viral activity, and against infection of the placenta; as well as antibodies against the interferon proteins.

17 Claims, 7 Drawing Sheets

OTHER PUBLICATIONS

E. R. Unanue et al., Antigen Presentation: Comments on Its Regulation and Mechanism, The Journal of Immunology 132:1, pp. 1–5.

D. Wallach et al., Preferential Effect of γ Interferon on the Synthesis of HLA Antigens and their mRNAs in Human Cells, Nature, 229, pp. 833–836.

D. A. Weigent et al., Recombinant Gamma Interferon Enhances Natural Killer Cell Activity Similar to Natural Gamma Interferon, Biochemical and Biophysical Research Communications, 111:2, pp. 525–529.

F. Aiuti et al., Identification, Enumeration, and Isolation of B and T Lymphocytes from the Human Peripheral Blood, (W.H.O. Workshop, 1974), Scandinavian Journal of Immunology, 3, pp. 521–532.

Aboagye–Mathiesen et al, "Purification of human placenta trophoblast ... higher performance liquid chromotography", Prep. Biochem, vol. 21 (1)pp. 35–51 (1991). (Abstract).

M. K. Rosenblum et al., Growth Inhibitory Effects of Interferon–β but Not Interferon–α on Human Glioma Cells: Receptor Binding, 2',5'–Oligoadenylate Synthetase and Protein Kinase Activity, Journal of Interferon Research, 10:141–151, (1990).

Irene Athanassakis, et al., The Immunostimulatory Effect of T Cells and T Cell Lymphokines on Murine Fetally Derived Placental Cells, The Journal of Immunology, 138, pp. 37–44, (1987).

F. Dianzani et al., A New Type of Human Interferon Produced by Peripheral Blood Mononuclear Cells Treated with Inhibitors of Transcription, Journal of Interferon Research, 6, pp. 43–50, (1986).

G. C. Douglas et al., Isolation of Pure Villous Cytotrophoblast from Term Human Placenta Using Immunomagnetic Micropheres, Journal of Immunological Methods, 119, pp. 259–268, (1989).

Gordon C. Douglas et al., Differentiation of Human Trophoblast Cells in Vitro as Revealed by Immunocytochemical Staining of Desmoplakin an Nuclei, Journal of Cell Science, 96, pp. 131–141, (1990).

Susan J. Fisher et al., Adhesive and Degradative Properties of Human Placental Cytotrophoblast Cells in vitro, The Journal of Cell Biology, 109, pp. 891–902, (1989).

A. G. Howatson et al., Localization of α–Interferon in the Human Feto–Placental Unit, Journal of Endocrinology, 119, pp. 531–534, (1988).

U. K. Laemmli, Cleavage of Structural Proteins during the Assembly of the Head Bacteriophage T4, Nature, 227, pp. 680–685, (1970).

P. Lebon et al., The Presence of α–Interferon in Human Amniotic Fluid, Journal of Virology, 59, pp. 393–396, (1982).

Tim Mosmann, Rapid Colorimetric Assay for Cellular Growth and Survival: Application to Proliferation and Cytotoxicity Assays, Journal of Immunological Methods, 65, pp. 55–63, (1983).

F. D. Toth et al., Interferon Production by Cultured Human Trophoblast Induced with Double Stranded Poly–ribonucleotide, Journal of Reproductive Immunology, 17, pp. 217–227, (1990).

Paulette Duc–Goiran et al., Unusual Apparently Constitutive Interferons and Antagonist in Human Placental Blood, Proceedings of the National Academy of Science U.S.A., 82, pp. 5010–5014, (1985).

J. O. Klein et al., An Introduction to Infection of the Fetus and Newborn Infant, Infectious Disease of the Fetus and Newborn, pp. 1–32.

P. B. Fisher et al., Effects of Interferons on Differentiation of Normal and Tumor Cells, Pharmacology and Therapeutics, 27, pp. 143–166.

Terry W. Chin et al., Enhanced Interferon Production and Lymphokine–activated cytotoxicity of human placenta cells, Cellular Immunology, 113, pp. 1–9.

Rudolf Hauptmann et al., A Novel Class of Human Type I Interferons, Nucleic Acids Research, 13, pp. 4739–4749.

J. C. Correttini et al., Inhibitory Effect of Interferon Preparations and Inducers on Multiplication of Transplanted Allogenic Spleen Cells and Syngeneic Bone Marrow Cells, Nature, London 242, pp. 152–153.

T. Chard et al., Alpha Interferon in Human Pregnancy, British Journal of Obstetrics and Gynaecology, 93, pp. 1145–1149.

Daniel J. Capon et al., Two Distinct Families of Human and Bovine Interferon–α Genes are Cordinately Expressed and Encode Functional Polypeptides, Molecular and Cellular Biology, 5, pp. 768–779.

John N. Zullo et al., Platelet–Derived Growth Factor and Double–Stranded Ribonucleic Acids Stimulate Expression of the Same Genes in 3T3 Cells, Cell, 43, pp. 793—800.

Terri Yamauchi, M. D. et al., Transmission of Live, Attenuated Mumps Virus to the Human Placenta, The New England Journal of Medicine, 290, pp. 710–712.

Miles Wilkinson et al., Interferon wwith Novvel Characteristics Produced by Human Mononuclear Leukocytes, Biochemical and Biophysical Research Communications, 111, pp. 498–503.

S. Sekiya et al., Effects of Human Interferons on Human Choriocarcinoma Cells in Vitro and in Vivo, Gynecologic Oncology, 25, pp. 115–124.

Larry E. Mobraaten et al., Prolongation of Allograft Survival in Mice by Inducers of Interferon, Transplantation, 16, pp. 415–420.

Martin S. Hirsch et al., Immonosuppressive Effects an Interferon Preparation in Vivo, Transplantation, 17, pp. 234–236.

Derek C. Burke et al., Appearance of Interferon Inducibility and Sensitivity during Differentiation of Murine Teratocarcinoma Cells in Vitro, Cell, 13, pp. 243–248.

Marion M. Bradford, A Rapid and Sensitive Method for the Quantitation of Microgram Quantities of Protein Utilizing the Principle of Protein–Dye Binding, Analytical Biochemistry, 72, pp. 248–254.

V. Bocci et al., The Physiological Interferon Response: IV Production of Interferon by the Perfused Human Placenta at Term (42155), Proceedings of the Society for Experimental Biology and Medicine, 180, pp. 137–143.

Gunther R. Adolf, Antigenic Structure of Human Interferon w1 (Interferon $_{\alpha_{11}}$1): Comparison with Other Human Interferons, Journal General Virology, 68, 1669–1676.

Corrado Baglioni, Interferon–Induced Enzymatic Activities and Their Role in the Antiviral State, Cell, 7, pp. 255–264.

Isabelle Marie et al., Differential Expression and Distinct Structure of 69–and 100–kDa Forms of 2–5A Synthetase in Human Cells Treated With Interferon, The Journal of Biological Chemistry, 265, pp. 18601–18607.

Judith N. Bulmer et al., Expression of the Proliferation Markers Ki67 and Transferrin Receptor by Human Trophoblast Populations, Journal of Reproductive Immunology, 14, pp. 291–302.

Ross S. Berkowitz, MD. et al., Effects of Products of Activated Leukocytes (Lymphokines and Monokines) on the Growth of Malignant Trophoblast Cells in Vitro, American Journal of Obstetrics and Gyneacology, 158, pp. 199–203.

George Aboagye–Mathiesen et al., Purification of Human Placental Trophoblast Interferon by Two–Dimensional High Performance Liquid Chromatography, Preparative Biochemistry, 21, pp. 35–51.

George Aboagye–Mathiesen et al., Purificatio and Initial Characterization of Human Placental Trophoblast Interferon Induced by Polyriboinosinic Polyribocytidylic Acid, Journal of General Virology, 71, pp. 3061–3066.

Jack S. Remington, M. D. et al., Toxoplasmosis, Infectious Disease of the Fetus and Newborn, pp. 89–195.

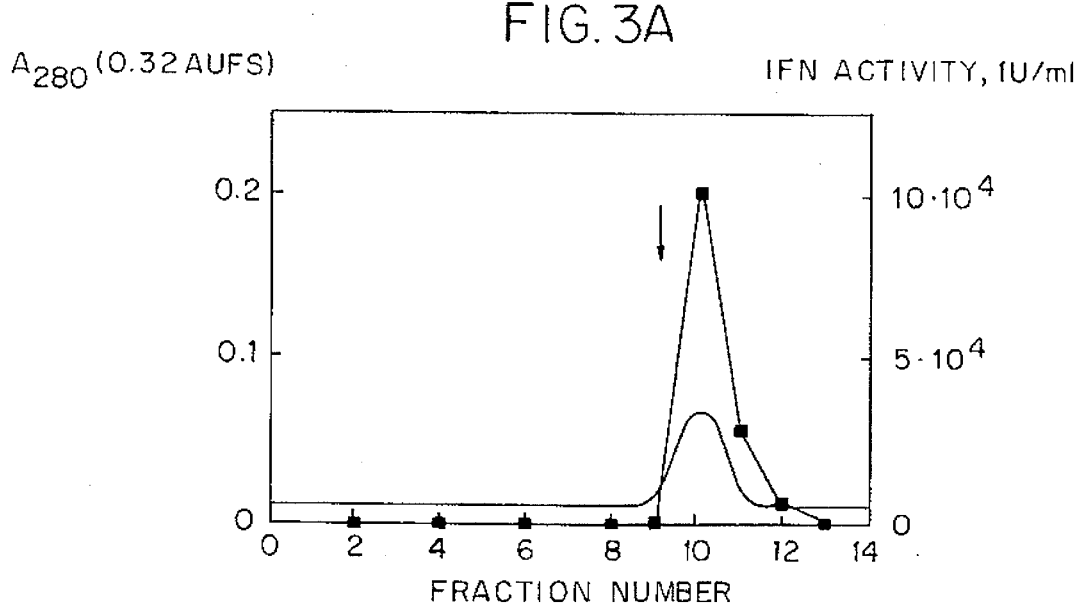
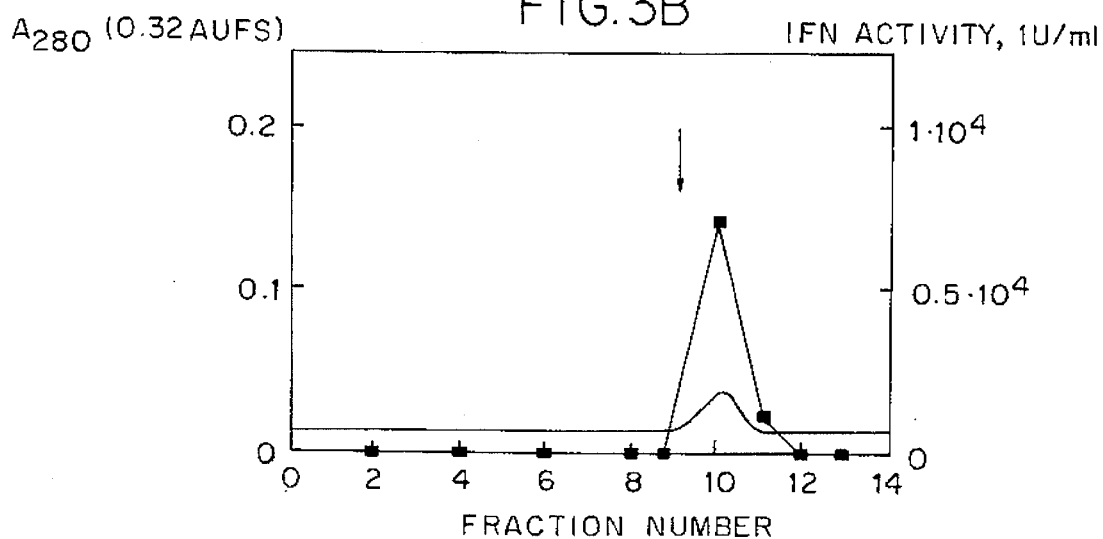
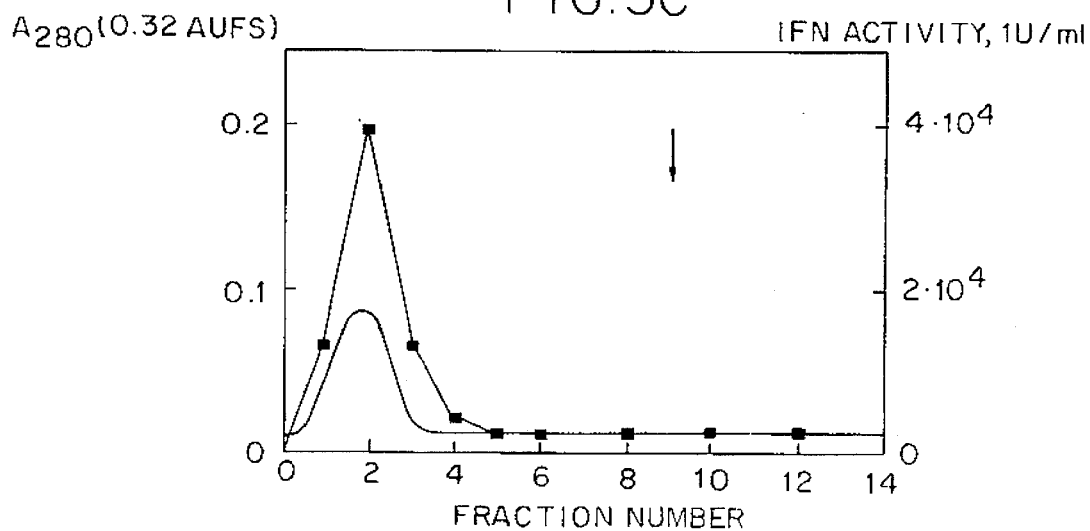

INTERFERON PROTEINS

The present invention relates to novel interferon proteins, their preparation, and their use, as well as antibodies against the interferon proteins.

The invention is based on the discovery that human trophoblasts produce proteins which conform with the internationally accepted characterizations of interferons, but which show properties indicating that they are not identical with known interferons, and on the isolation and characterization of the trophoblast-produced interferons. Thus, the interferon proteins of the invention are human interferon proteins/glycoproteins produced by human trophoblasts, or the same or substantially the same proteins when produced by other means, such as by recombinant techniques. The invention relates to these proteins when existing outside their natural environment, in other words in non-naturally occurring forms, e.g. as homogeneous proteins, or in purified or pure or substantially pure form, such as disclosed herein. The invention also provides methods for producing these novel proteins by cell cultivation and protein purification, including methods for production in a scale which makes it possible to use the interferon proteins for prophylactic and therapeutic treatment of humans and other warm-blooded animals, and in a scale which is realistic for the establishment of the amino acid sequence of the interferon proteins as well as the sequence of DNA coding for the proteins.

As described in the following, substantially pure human trophoblast interferon proteins/glycoproteins have been isolated by two-dimensional high performance liquid chromatography and other methods suitable for production in quantities sufficient for prophylactic or therapeutic treatment of humans or other warm blooded animals.

The properties of the novel interferon proteins combined with the fact that the invention makes it possible to produce them in large quantities will make it possible to use them, e.g., in the following applications:

- Prevention of virus, in particular human immunodeficiency virus and herpes simplex virus, from infected mother to noninfected fetus during pregnancy and during labour,
- treatment of virus and non-virus infections of the placenta, such as treatment of the fetal membranes, treatment via the amnion fluid, and treatment of the fetus in cases where acute systemic maternal infections are diagnosed,
- treatment of benign and malignant tumors (choriocarcinomas) arising from the placenta,
- identification of the trophoblast-produced interferons in amnion fluid, and maternal blood, using, e.g., antibodies according to the invention, can be used as a signal of disease, as well as a number of other applications as explained in the following.

The human trophoblast interferons of the present invention are products of the isolated first and term placenta non-MHC carrying villous trophoblasts. They are compounds which, being interferon, per definition have antiviral activity, but which in addition have been found to show ability to inhibit tumour cell growth and modulate immune responses.

BACKGROUND ART

Interferons are characterised as alpha class I, alpha class II, beta and gamma interferons as determined by inactivation of the antiviral effects with internationally accepted standard antibodies. Trophoblast-produced interferons are also, according to international rules, designated trophoblast interferons. A number of interferons derived from trophoblasts of non-human animals such as sheep and cattle, are known.

The known trophoblast interferons have been implied to be cytokines with an autocrine influence on differentiation of the normal trophoblasts, defence against virus infections, regulation of cell division and modulation of maternal immune attacks against the fetal tissues.

Several groups have demonstrated alpha interferon in amnion fluid, placenta tissue and cord blood, (Lebon et al. 1982,, DucGoiran et al. 1985, Chard et al. 1986) even from apparently uninfected term used placenta (Bocci et al, 1985). The cell(s) of origin and chemical composition except for neutralization by anti-interferon alpha antibodies was not delineated in these studies. Immunochemistry furthermore showed human trophoblasts to harbour alpha (Howatson et al., 1988). Earlier studies also showed animal trophoblasts capable of in vitro production of interferons (Godkin et al., 1982).

It had been reported that purified human villous trophoblasts isolated by negative selection (non MHC-1, A, B, C expression) may produce interferon in vitro. Term placenta trophoblasts were exposed to polyriboinosinic-polyribocytidylic acid (poly 1:C) which led to production of beta type interferon activity (Toth et al., 1990).

However, until the present invention, no interferon definitely shown to be produced by human trophoblasts had been isolated and characterized, and there was no indication that the interferons produced by human trophoblasts are different from known interferons.

DISCLOSURE OF THE INVENTION

The present invention provides a number of isolated and characterized novel human trophoblast-produced interferons. These interferons are not only β-interferon, but also $\alpha_I$-interferon, $\alpha_{II}$-interferon, and γ-interferon. The invention also relates to methods for producing, isolating and purifying the novel interferons. Furthermore, the realization and understanding of the character of the human trophoblast-produced interferons makes it possible to devise a number of important uses of the interferons, not only for purposes established for known human interferons, but also for a number of purposes related to the fact that the interferons are produced by and characteristic of trophoblast cells, their environment, and their function.

Generally, the production of human trophoblast interferons according to the invention is normally based on establishment of primary cultures of isolated human trophoblast, stimulation with chemical or virus and subsequent recovery of interferons from the culture medium. Particular embodiments include, e.g., the following:

1) The human placenta material is chemically minced and enzymatically digested. The resulting cell suspension is density gradient centrifuged and the harvested band is exposed to negative selection with magnetic beads carrying antibodies removing cells expressing the major histocompatibility complex MHC-1. Residual cells after test for purity are seeded.

2) Stimulation of seeded cells with the synthetic double stranded RNA Poly I:C or the RNA Sendai virus or Newcastle Disease virus.

3) Immobilization of Cibacron Blue F 3GA on HEMA-BIO 1000 VS (see FIG. 7 and Example 2) via a spacer arm, 1,4-diaminobutane, and immobilization of anti interferon alpha and beta on HEMA 1000 VS, thereby creating new types of very efficient adsorbents for interferon purification under High performance conditions, that is, under HPLC conditions.

4) Tandem high-performance affinity chromatography where the interferon absorbed to HEMA-BIO 100 VST 3GA was eluted into HEMA 1000 VS-antiIFN-beta and HEMA 1000 VS-anti-1FN-alpha. Interferons bound to these two columns were eluted separately.

The present invention is additionally directed to a method for protecting human placenta and human fetus against infection with the human immunodeficiency virus (HIV) during pregnancy and protection of the human fetus against infection with a virus such as HIV and Human Herpes vira such as Herpes Simplex virus or cytomegalovirus during labour.

The results presented in the examples herein show that trophoblast cultures infected, e.g., with Sendai virus produce a mixture of $\alpha_I$-interferon, $\alpha_{II}$-interferon, $\beta$-interferon; the interferon production increased after differentiation of the cytotrophoblast to syncytiotrophoblast in vitro (Toth et al, 1990). Similarly, Burke et al, (1978) have reported that the production of interferon and interferon sensitivity change during differentiation of mouse embryonal carcinoma in vitro.

The trophoblast interferons ($\alpha_I$, $\alpha_{II}$, $\beta$) are antigenically distinct which is an indication that they are structurally different. Antiserum to human $\alpha_{II}$-interferon could not neutralize trophoblast $\alpha_I$-interferon component (fractions 21 to 40 from FIG. 1) or trophoblast $\beta$-interferon but completely neutralized trophoblast $\alpha_{II}$-interferon purified by HP-IAC. The ability of polyclonal anti-human $\beta$-interferon (lymphoblastoid) to neutralize both the antiviral activities of trophoblast $\alpha_I$-interferon and trophoblast $\alpha_{II}$-interferon can be explained by the fact that $\alpha_{II}$-interferon is a component of natural mixtures of lymphoblastoid and leukocyte IFN preparations (Adolf, 1987) used to prepare polyclonal antibodies. The neutralization results support the suggestion (Adolf, 1987) that human type 1 interferon is made up of three antigenically distinct proteins, $\alpha_I$-interferon, $\alpha_{II}$-interferon and $\beta$-interferon.

The response of different cell lines to the antiviral effects of the trophoblast interferons when tested by inhibition of plaque formation varied. The results presented in Table 4 show that the trophoblast interferons differ from one another in their ability to confer protection against VSV infection of different human and bovine cell species. Trophoblast $\beta$-interferon showed a degree of species specificity, protecting human cells but not bovine (MDBK) cells. However, the trophoblast $\alpha_I$-interferon and trophoblast $\alpha_{II}$-interferon protect both human and bovine cells. The variations in the relative antiviral activities of trophoblast interferons in the different cells may indicate that they differentially affect biochemical pathways induced by interferons, such as phosphorylation of the eukaryotic initiation factor-2 (eIF- 2) by the double-stranded (ds) RNA-dependent protein kinase or activation of 2'- 5'-oligoadenylate-system (Marié et al., 1990; Baglioni, 1979). That interferons differentially induce biochemical pathways which correlate with particular specific antiviral activities in various lines of cells is indicated by studies with different interferon preparations (Rosenblum et al., 1990). Differences between distinct interferons or between distinct cell types may be of importance for the therapeutic application of interferons, particularly when such differences occur within the same organism.

The human placenta is important from a pharmacological and virological perspective, since among its numerous functions it also acts as a selective barrier to virus traffic to the foetus. The fetal-placental unit depends on the unique functional and structural characteristics of the placental syncytiotrophoblast which is in direct contact with maternal blood and forms a continuous layer that mediates the interaction between maternal and fetal components (Douglas and King, 1990).

In the first trimester, the cytotrophoblasts are highly proliferative and invasive and undergo a series of differentiation to form a multinuclear syncyntiotrophoblast that displays little potential to proliferate. The balance between proliferation and differentiation determines the structure and function of the trophoblast and its "pseudomalignant" properties. The processes underlying the morphological transformation are, however, presently not well understood.

Cytokines, such as interferons, interleukins and tumour necrosis factor may play an important role in regulating the growth and differentiation of trophoblast cells as demonstrated (Berkowitz et al., 1988; Athanassakis et al., 1987) to stimulate or inhibit the proliferation of malignant human trophoblast.

One aspect of the biochemical differentiation of cytotrophoblast is demonstrated in vitro in Example 5 herein by demonstrating differential interferon production in first and third trimester trophoblast cultures stimulated with mitogens and viruses. It was found that the first trimester trophoblast stimulated with different inducers led to enhanced production of interferons compared to the third trimester trophoblast.

The trophoblast layer of the human placenta constitutes the maternal-fetal interface and acts as a barrier to the transmission of infection from mother to fetus. The ability of trophoblast cells to produce interferons may represent a system for the protection of the fetus from viral infection. This is shown by the fact that, in some cases, maternal infection may spread to the placenta but fail to progress to the foetus (Yamauchi et al., 1974; Klein et al., 1976; Remington & Desmonts, 1976). In addition to the antiviral activity of interferons, there is increasing evidence that interferons are also involved in the normal physiological and regulatory processes such as cell proliferation and differentiation (Zullo et al., 1985; Fisher & Grant, 1985). Cells of the cytotrophoblast have been shown (Bulmer et al., 1988) to be highly proliferative, as measured by the proliferative marker Ki67 or the presence of mitoses, but lose their proliferative activity and begin to differentiate as they migrate into ducidua during implantation. Although the factors that control such aspects of trophoblast behaviour are not known, interferons may play a major role in the development of these differentiated states. Furthermore, the $\alpha$-interferon has been shown to be involved in prolongation of allograft survival (Hirsch et al., 1974; Mobraaten et al., 1973) and suppression of graft-versus-host disease (Corettini et al., 1973). Such modulation of the immune response by interferon may be important in the rejection of the allogenic fetus.

As indicated above, the production and characterization of the novel interferons, as well as the fact the effective methods for producing the interferons disclosed herein, make it possible to obtain high amounts of the novel interferons in extremely high purity, which, inter alia, can be utilized for amino acid sequencing and DNA sequencing purposes, as well as for the establishment of antibodies. Thus, the invention relates not only to the novel interferons when produced by human trophoblasts, but also to the identical or substantially identical interferon proteins when produced by other means using, e.g, recombinant technique.

Thus, in one aspect, the invention relates to an isolated interferon protein which is identical or substantially identical to a human interferon protein which is produced by a human trophoblast cell and which is characterized as a β-interferon which is produced by a term trophoblast cell or a trophoblast cell derived from a provoked vaginal delivery, which trophoblast cell is a villous trophoblast which did not bind by magnetic beads carrying immobilized antibodies to the tissue types MHC-1, A, B, or C, the β-interferon being obtainable in purified form from a filtered (0.22 μm filter) supernatant of a stimulated culture of the trophoblast cells, by a purification scheme comprising either 1) High-performance dye-ligand affinity chromatography followed by applying the thus obtained interferon-containing fractions to High-performance immunoaffinity chromatography using immobilized anti-β-interferon antibodies or 2) High-performance dye-ligand chromatography followed by Reversed phase HPLC, the β-interferon possessing at least one of the following characteristics i–iv:

i) the β-interferon in purified form appears substantially as only one silver-stainable band showing antiviral activity with a molecular weight in the range of 22–26 kDa, in a slab SDS-PAGE, applying an amount of 25 β-interferon of 40.000 IU, under reducing conditions using 5% 2-mercaptoethanol or under non-reducing conditions without using 2-mercaptoethanol, ii) the antiviral activity of the β-interferon, as measured by inhibition of vesicular stomatitis virus plaque formation in a human amniotic cell line WISH cells (ATCC, CCL 25), is retained in a pattern which resembles the specific pattern of retainment to an extent of about 55% of the initial value of antiviral activity after 3 hours at a temperature of 37° C., and to an extent of about 45–55%, in particular about 48–52% after 10 minutes at a temperature of 56° C., 38–47%, in particular about 41–45%, after 15 minutes at a temperature of 56° C., 0–10%, in particular about 1–5%, after 60 minutes at a temperature of 56° C., iii) the β-interferon substantially retains its antiviral activity after storage in 0.1M glycine at pH 2 for 24 or even 48 hours, as measured by inhibition of the plaque formation in human amniotic cell line WISH caused by vesicular stomatitis virus (VSV), Indiana strain, iv) the β-interferon shows a high degree of hydrophobicity as indicated by it requiring a concentration of 50% of the hydrophobic eluent ethylene glycol in 0.02M sodium phosphate buffer pH 7.2 containing 1.0M NaCl to be eluted from the High performance dye-ligand affinity chromatography column.

The above-mentioned isolation and purification methods are, of course, not the only available methods for isolating and purifying the β-interferon protein according to the invention, but they have been found to be highly useful and efficient methods for the purpose and, thus, well suited for defining the purified forms of the β-interferon. The exact manner in which the isolation and purification may be performed using these methods appears from the below disclosure and the examples, where the unique novel HEMA adsorbents are used both for the High performance dye-ligand chromatography and for the High performance immunoaffinity chromatography.

The purity obtainable by either of the above-mentioned purification schemes is normally sufficient to ensure that the β-interferon will appear substantially as only one silver-stainable band showing antiviral activity with a molecular weight in the range of 23–25 kDa, in particular at 24 kDa, determined as described above.

For most purposes, it is preferred that the β-interferon protein according to the invention is in substantially pure form, such as in a purity of at least 95%, preferably at least 99%, as measured by densitometric scanning of a Coomassie Blue gel at 595 nm.

As appears from Example 3, a purity of at least 95% of the β-interferon according to the invention, as measured by densitometric scanning of a Coomassie Blue gel at 595 nm, has been obtained by subjecting the β-interferon to high performance dye-ligand affinity chromatography, and a combination of high performance dye-ligand chromatography and subsequent high performance immunoaffinity chromatography using immobilized anti-β-interferon antibodies has resulted in a purity of at least 99%, as measured by densitometric scanning of a Coomassie Blue gel at 595 nm.

As appears from Example 3, the specific activity of the β-interferon of the invention has been found to be at least about $1.0 \times 10^8$ IU/mg of protein when the interferon is in a purified form.

Whether the β-interferon of the invention is in a purified form or not, it has a high temperature stability, such as appears from characteristic ii) above (Example 3). This temperature stability pattern is different from the temperature stability patterns of known human fibroblast interferons induced by poly(rI).poly(rC) or virus which have been reported to have half lives in the range of 2 to 7 minutes.

One interesting characteristic of the β-interferon protein according to the invention is that it is capable of protecting human cell lines WISH (ATCC), GM 2504 and GM 2767 trisomy 21 fibroblasts (cell Repository, Cambden, N.J., U.S.A.) against an infection with vesicular stomatitis virus (VSV), Indiana strain, but is not capable of protecting bovine cell line MBDK against a vesicular stomatitis virus (VSV), Indiana strain, infection, such as appears from Table 3 (Example 3).

As shown in Example 2, the β-interferon produced by the human trophoblast cells binds to Concanavalin A and hence, is a glycoprotein. When produced by recombinant DNA technique in bacteria in analogy with the known production of known interferons, the β-interferon protein according to the invention will be obtained in unglycosylated form. The invention comprises both the glycosylated and the unglycosylated form.

In another aspect, the invention relates to an isolated interferon protein which is identical or substantially identical to a human interferon protein which is produced by a human trophoblast cell and which is characterized as an $\alpha_f$-interferon which is produced by a term trophoblast cell or a trophoblast cell from a provoked vaginal delivery, which trophoblast cell is a villous trophoblast which does not bound by magnetic beads carrying immobilized antibodies to the tissue types MHC-1, A, B, or C, the $\alpha_f$-interferon being obtainable in purified form from a filtered (0.22 μm filter) supernatant of a stimulated culture of the trophoblast cells by a purification scheme comprising either 1) High-performance dye-ligand affinity chromatography followed by applying the thus obtained interferon-containing fractions to High-performance immunoaffinity chromatography using immobilized anti-$\alpha_f$-interferon antibodies or 2) High-performance dye-ligand chromatography followed by Reversed phase HPLC, the $\alpha_f$-interferon possessing at least one of the following characteristics i–iii:

i) the $\alpha_I$-interferon in purified form appears substantially as only one silver-stainable band showing antiviral activity with a molecular weight in the range of 15–20 kDa in a slab SDS-PAGE, applying an amount of $\alpha_I$-interferon of about 45.000 IU, under reducing conditions using 5% 2-mercaptoethanol or under non-reducing conditions without using 2-mercaptoethanol, ii) the $\alpha_I$-interferon substantially retains its antiviral activity after storage in 0.1M glycine at pH 2 for 24 hours measured by inhibition of the plaque formation in human amniotic cell line WISH (ATCC) caused by vesicular stomatitis virus (VSV), Indiana strain, iii) the $\alpha_I$-interferon is bound to the High performance dye-ligand chromatography column by electrostatic forces as evidenced by its ability to be displaced from the column by the ionic salt NaCl.

What has been stated above in connection with the β-interferon according to the invention with respect to isolation and purification, purity, and purity percentage, also applies to the $\alpha_I$-interferon according to the invention, the SDS band characteristic to this interferon, however, corresponding to a molecular weight of 15–17 kDa, in particular 16 kDa, determined as described above.

One interesting characteristic of the $\alpha_I$-interferon protein according to the invention is that it is capable of protecting the human cell lines WISH (ATCC), GM 2504 and GM 2767 trisomic 21 fibroblasts (Cell Repository, Cambden, N.J., USA) against a viral infection with vesicular stomatitis virus (VSV), Indiana strain, and which is capable of protecting the bovine cell line MDBK against a vital infection with vesicular stomatitis virus (VSV), Indiana strain, to a higher extent than it protects the human cell line WISH, such as described in Example 3.

As shown in Example 3, the human trophoblasts produce the $\alpha_I$-interferon in unglycosylated form.

In a further aspect, the invention relates to an isolated interferon protein which is identical or substantially identical to a human interferon protein which is produced by a human trophoblast cell and which is characterized as an $\alpha_{II}$-interferon which is produced by a term trophoblast cell or a trophoblast cell derived from a provoked vaginal delivery, which trophoblast cell is a villous trophoblast which does not bound by magnetic beads carrying immobilized antibodies to the tissue types MHC-1, A, B, or C, the $\alpha_{II}$-interferon being obtainable in purified form from a filtered (0.22 μm filter) supernatant of a stimulated culture of the trophoblast cells by a purification scheme comprising either 1) High-performance dye-ligand affinity chromatography followed by applying the thus obtained interferon-containing fractions to High-performance immunoaffinity chromatography using immobilized anti-$\alpha_{II}$-interferon antibodies or 2) High-performance dye-ligand chromatography followed by Reversed phase HPLC, the $\alpha_{II}$-interferon possessing at least one of the following characteristics i–iii:

i) the $\alpha_{II}$-interferon in purified form appears substantially as only one silver-stainable band showing antiviral activity with a molecular weight in the range of 20–24 kDa, in a slab SDS-PAGE, applying an amount of $\alpha_{II}$-interferon of about 45.000 IU, under reducing conditions using 5% 2-mercaptoethanol or under non-reducing conditions without using 2-mercaptoethanol, ii) the $\alpha_{II}$-interferon substantially retains its antiviral activity after storage in 0.1M glycine at pH 2 for 24 hours measured by inhibition of the plaque formation in human amniotic cell line WISH (ATCC) caused by vesicular stomatitis virus (VSV), Indiana strain, What has been stated above in connection with the β-interferon according to the invention with respect to isolation and purification, purity, and purity percentages, also applies to the $\alpha_I$-interferon according to the invention, the SDS band characteristic of this interferon, however, corresponding to a molecular weight of 21–23 kDa, in particular 22 kDa, determined as described above.

One interesting characteristic of the $\alpha_{II}$-interferon protein according to the invention is that it is capable of protecting human cell lines WTSH (ATCC), GM 2504 and GM 2767 trisomy 21 fibroblasts (Cell Repository, Cambden, N.J., U.S.A.) against an infection with vesicular stomatitis virus (VSV), Indiana strain, and not capable of protecting bovine cell line MBDK against a vesicular stomatitis virus (VSV), Indiana strain, infection, to a higher degree than it protects the human cell lines, such as appears from Table 3 (Example 3).

In a still further aspect, the invention relates to an isolated interferon protein which is identical or substantially identical to a human interferon protein which is produced by a human trophoblast cell and which is characterized as a γ-interferon which can be obtained from a first trimester trophoblast cell from a provoked vaginal delivery, which trophoblast cell is a villous trophoblast which does not bound by magnetic beads carrying immobilized antibodies to the tissue types MHC-1, A, B, or C, the γ-interferon being obtainable in purified form from a stimulated culture of the trophoblast cells by the following purification scheme comprising High-performance dye-ligand affinity chromatography followed by binding to immobilized Concanavalin A and subsequent displacement with a sugar and then controlled pore glass affinity chromatography. This interferon is not stable at pH 2 under the conditions described above where the above-mentioned interferons are stable.

A component of the β-interferon fractions from the High performance dye-ligande chromatography has cytotoxic effect as determinable by standard methods, such as test for influence on the metabolic reduction of 3-(4,5-dimethylthiazol- 2-yl)-2,5-diphenyl-tetrazolium bromide (MTT test), and each of the interferons has antiproliferal effect as determinable by standard methods, such as assay of [$^3$H] thymidine incorporation in vitro.

Based upon observations to the effect that a human trophoblast cell derived from abortion placentas of 5 to 12 weeks of age was capable of producing antiviral activity which could not be associated with any of the established human interferon classifications, it is justified to assume that the human trophoblast cells at this particular very early stage and earlier are capable of producing a special novel type of interferon, the function of which may conceivably be the same as the function of corresponding interferons ("trophoblast proteins", TP) produced in certain non-human animals, that is, as fertility enhancers which also have antiviral activity, in particular as a compound influencing the uterine epithelium, corpus lutea and the pituitary gland to the effect of maintaining the progesteron level and/or modulate the local maternal immunologic and nonimmunologic response to the fetal allograft. Furthermore, the human trophoblasts are likely to be capable of producing interferon related to the known interferon beta 2 (interleukin 6).

Thus, this aspect of the invention relates to an interferon which is produced by a human trophoblast cell derived from abortion placentas of 5 to 12 weeks of age, which trophoblast cell is a villous trophoblast which is not bound by magnetic beads carrying immobilized antibodies to the tissue types MHC-1, A, B, or C, the interferon being obtainable in purified form from the supernatant of a stimulated culture of the trophoblast cells by the following purification schemes comprising 1) High-performance dye-ligand affinity chromatography, the interferon not pertaining to any of the interferon classes $\beta$, $\alpha_I$, $\alpha_{II}$ and $\gamma$.

As explained above, apart from the $\beta$-interferon activity reported in Toth et al., 1990, human trophoblast interferons, whether isolated/purified or not, are believed never previously, prior to the present invention, to have been produced by culturing human trophoblast cells in vitro. According to the present invention, it has been found that by suitable stimulation, other interferons identified and characterized above are produced by human trophoblasts.

Thus, one aspect of the invention relates to a method for producing an interferon selected from $\gamma$-interferon, $\alpha_I$-interferon, and $\alpha_{II}$-interferon from human trophoblasts, comprising cultivating the human trophoblast, and stimulating the culture with an agent capable of inducing the production of an interferon selected from $\gamma$-interferon, $\alpha_I$-interferon, and $\alpha_{II}$-interferon.

However, for all practical considerations, the process aspect of the present invention is one in which the inteferon or interferons produced is/are obtained and isolated from the culture. Thus, this aspect can be expressed as a method for producing an interferon or interferons selected from $\beta$-interferon, $\alpha_I$-interferon and $\alpha_{II}$-interferon and $\gamma$-interferon from human trophoblasts, comprising cultivating the human trophoblast, stimulating the culture with an agent capable of inducing the production of an interferon selected from $\beta$-interferon, $\alpha_I$-interferon, $\alpha_{II}$-interferon and $\gamma$-interferon, and isolating the interferon or interferons from the culture.

Stimulating agents which have been found, according to the invention, to stimulate the production of these interferons by trophoblasts, are virus, synthetic double stranded RNA, interleukins, plant mitogens, and growth factors. Thus, e.g., a very suitable stimulating agent for producing $\gamma$-interferon is a plant mitogen and/or a cytokine. In particular, an effective stimulating agent for producing $\gamma$-interferon is a combination of phytohaemagglutinin and interleukin-2, such as a combination of 50–200 U/ml, e.g. 100 U/ml, of interleukin 2 together with 3–10 µg/ml, such as 5 µg/ml, of phytohaemagglutinin, Other stimulating agents suitable for inducing the in vitro production of the above-mentioned interferons by human trophoblasts are Concanavalin A, lipopolysaccharide, pock wheat mitogens and 4-$\beta$-phorbol-12-$\beta$-myristate-13-$\alpha$-acetate.

As appears from Example 5, stimulation with different virus can result in differences in the composition of the interferons produced. It is also important to note that Example 5 demonstrates that first trimester trophoblasts (5 to 12 weeks) yield 5–7 times higher interferon yields than third trimester trophoblasts.

According to a particular aspect of the invention, the interferon production by the stimulated culture of human trophoblast cells is increased when the culture is kept under an oxygen-containing atmosphere. In this aspect, the invention relates to a method for producing a human trophoblast interferon, comprising cultivating human trophoblast cells under an oxygen-containing atmosphere, stimulating the culture with an agent capable of inducing the production of interferon, and obtaining interferon from the culture.

The oxygen-enriched atmosphere is suitably nitrogen with about 2–10%, such as 3–7%, e.g. 5%, of oxygen.

According to the invention, human trophoblasts have been found to vary with their development stage with respect to their capability of producing a particular interferon. Thus, e.g., human $\gamma$-interferon is produced by the trophoblast cells at a rather early stage of development. These cells, when obtained by normal means, such as described herein, will tend to attach, together with other cells and other types of sort to surfaces in the vessels in which they are cultured. According to an aspect of the invention, however, it is possible to substantially selectively loosen or free these trophoblast cells from the surface, leaving the other cell still bound to the surface, thus obtaining, in the culture medium, a substantially pure population of these trophoblast cells.

Thus, in one aspect, the invention relates to a method of producing an interferon protein according to the invention, from trophoblast cells in a culture which, in addition to the trophoblast cells, contains other cells and which grows in a culture attached to a surface, the method comprising treating the culture with a calcium binding chelator, isolating the cells thereby detached from the surface, culturing the thus isolated cells, stimulating the resulting trophoblast cell culture with an agent capable of stimulating an interferon production, and obtaining the interferon protein from the culture.

This method is especially effective and valuable when the culture is a culture obtained from a provoked first trimester vaginal delivery, the vaginal tissue typically being placental tissue which has been digested enzymatically, such as with trypsin, followed by pooling and gradient centrifugation. The temperature of the culture is preferably about 0° C. during the treatment with the calcium binding chelator. The calcium binding chelator is preferably EDTA, such as EDTA in a concentration of the about 0.02%. When the trophoblast cells have been liberated from the surface in this manner, they are suitably reseeded on a fresh culture medium.

In conformity with what is stated above in connection with the characterization and purity of the individual interferons, the generally preferred method of the invention for isolating and purifying an interferon produced by a human trophoblast cell culture comprises subjecting supernatant from the culture to affinity chromatography and obtaining, from the eluate from the chromatography, the fractions containing interferon activity. The affinity chromatography is preferably a high performance affinity chromatography selected from high performance dye-ligand affinity chromatography, high performance Concanavalin A affinity chromatography, high performance immunoaffinity chromatography, and Reversed phase HPLC. Evidently, in selecting the purification scheme, the stabilities of the interferons should be taken into consideration. Thus, e.g., $\gamma$-interferon, which is not stable at pH 2, should not be purified using immunoaffinity which involves exposure to such low pH.

Figure 7:
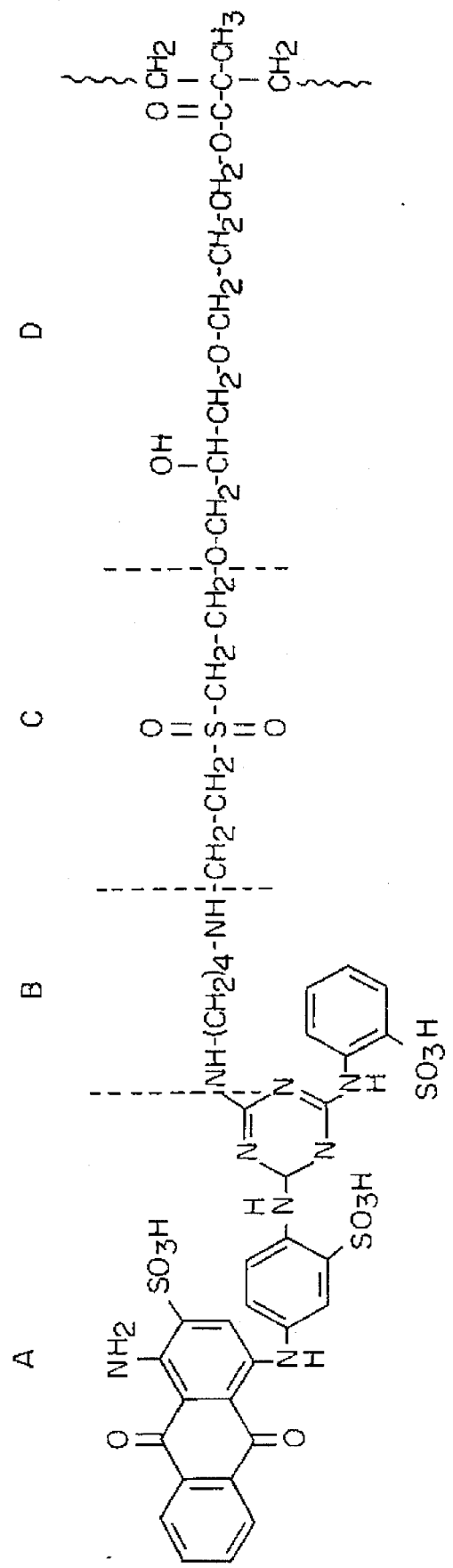

A particular aspect of the invention is the use of adsorbents based on the 2-hydroxyethyl methacrylate (HEMA) polymer to which a ligand has been bound, such as a dye, e.g. Cibachron Blue F 3GA, or antibodies, e.g. via a spacer arm such as explained in Example 2 and illustrated in FIG. 7. These adsorbents permit very high throughput and result in extremely high purifications of the interferons, such as is illustrated herein.

The invention also relates to a monoclonal or polyclonal antibody which binds to an interferon as defined above or a part thereof. A most useful type of antibody is a monoclonal antibody; however, also a polyclonal antibody may be of great importance provided it shows a sufficient selectivity, which may be obtained, e.g., by means of known absorption methods.

The term "antibody" refers to a substance which is produced by a mammal or more precisely a cell of mammalian origin belonging to the immune system as a response to exposure to the polypeptides or carbohydrates of the invention.

The variant domain of an antibody is composed of variable and constant sequences. The variant part of the domain defines the idiotype of the antibody. This part of the antibody is responsible for the interaction with the antigen, such as the interferon, and thereby the antigen binding.

The idiotypic structure is antigenic and can thus give rise to specific antibodies directed against the idiotypic structure. Production of such anti-idiotypic antibody can be done in mice. The antibodies raised against the idiotype, the anti-idiotypic antibodies, may mimic the structure of the original antigen and therefore may function as the original antigen to raise antibodies reactive with the original antigen. This approach may be advantageous as it circumvents the problem associated with the characterization and synthesis of the important immunogenic parts of the antigen in question. This is most important in the case of conformational epitopes, which might otherwise be difficult to identify. The present invention therefore also relates to an anti-idiotypic antibody which is directed against the site of an antibody which binds the antigen or the epitope according to the invention.

The antibodies of the present invention may be produced by a method which comprises administering in an immunogenic form at least a part of the interferon of the invention or an anti-idiotic antibody as defined above to obtain cells producing antibodies reactive with the interferon or a part thereof, and isolating the antibody containing material from the organism or the cells. The methods of producing antibodies of the invention will be explained further below.

The antibody of the invention may be used in an assay for the identification and/or purification and/or quantification of at least a form and/or a part of the interferon of the invention present in a sample. The identification and/or purification and/or quantification performed by the use according to the present invention may be any identification and/or purification and/or quantification involving the interferon of the invention. The identification and/or purification and/or quantification may be performed for both a scientific, a clinical and an industrial purpose, As will be further described below, it is especially important in clinical routine to identify or quantify antigens or epitopes of the invention.

The sample may be a specimen obtained from a living organism such as a human or an animal. The specimen may be a sample of body fluid, such as a blood sample, or a tissue sample.

In one preferred embodiment of the invention it is preferred that the antibody used in the method of the invention is a monoclonal antibody as this generally provides a higher precision and accuracy of the assay, at the same time possibly requiring less time to perform. Furthermore, a mixture of two or more different monoclonal antibodies may be employed as this may increase the detection limit and sensitivity of the test. The monoclonal antibody may be obtained by the method described below. Antibodies possessing high avidity may be selected for catching techniques.

The antibody used in the present method is preferably in substantially pure form (purified according to suitable techniques or by the methods of the invention, see below) in order to improve the precision and/or accuracy of the assays of the invention.

The determination of antibodies reactive with the interferon of the invention and being present in a sample, e.g. as defined above, may be carried out by use of a method comprising contacting the sample with the antibody of the invention and detecting the presence of bound antibody resulting from said contacting and correlating the result with a reference value.

When the antibody of the invention is to be employed in an assay for determining the presence of the interferon of the invention in a sample, it may be in the form of a diagnostic reagent or a diagnostic agent. As will be apparent to a person skilled in the art several techniques may be applied in connection with such diagnostic reagents.

Another field of the invention is a method for producing an antibody which binds to an interferon of the invention, which comprises immunizing an animal with an interferon or part thereof or an anti-idiotypic antibody or an interferon produced by cultivating cells harboring a plasmid which contains and is capable of expressing an interferon or part thereof as described above, whereby cells producing an antibody specific for the interferon or part thereof is obtained and the antibody is isolated from the animal or the cells.

The antibody is preferably a monospecific antibody. The monospecific antibody may be prepared by injecting a suitable animal with a substantially pure preparation of the interferon of the invention or a part thereof followed by one or more booster injections at suitable intervals (e.g. one or two weeks to a month) up to four or five months before the first bleeding. The established immunization schedule is continued, and the animals are bled about one week after each booster immunization, and antibody is isolated from the serum in a suitable manner (cf. e.g. Harboe and Ingild, *Scand, J. Immun.* 2 (Suppl. 1), 1973, pp. 161–164.)

For purposes not requiring a high assay specificity, the antibody may be a polyclonal antibody. Polyclonal antibodies may be obtained, e.g. as described in Harboe and Ingild, see above. More specifically, when polyclonal antibodies are to be obtained, the compound comprising an interferon of the invention or part thereof or an anti-idiotype antibody as described above is prepared and preferably after addition of a suitable adjuvant, such as Freund's incomplete or complete adjuvant, injected into an animal. The animals are bled regularly, for instance at weekly intervals, and the blood obtained is separated into an antibody containing serum fraction, and optionally said fraction is subjected to further conventional procedures for antibody purification, and/or procedures involving use of purified compounds comprising an interferon of the invention or a part thereof or an idio-typic antibody as described above.

In another preferred embodiment, monoclonal antibodies are obtained. The monoclonal antibody may be raised against or directed substantially against an essential component of the compounds comprising an interferon of the invention or a part thereof or an anti-idiotypic antibody as described above. The monoclonal antibody may be produced by conventional techniques (e.g. as described by Köhler and Milstein, Nature 256, 1975, p. 495) e.g. by use of a hybridoma cell line, or by clones or subclones thereof or by cells carrying genetic information from the hybridoma cell line coding for said monoclonal antibody. The monoclonal antibody may be produced by fusing cells producing the monoclonal antibody with cells of a suitable cell line, and selecting and cloning the resulting hybridoma cells producing said monoclonal antibody. Alternatively, the monoclonal antibody may be produced by immortalizing an unfused cell line producing said monoclonal antibody, subsequently growing the cells in a suitable medium to produce said antibody, and harvesting the monoclonal antibody from the growth medium.

The immunized animal used for the preparation of antibodies of the invention is preferably selected from the group consisting of rabbit, monkey, sheep, goat, mouse, rat, pig, horse and guinea pigs. The cells producing the antibodies of the invention may be spleen cells or lymph cells, e.g. peripheric lymphocytes.

When hybridoma cells are used in the production of antibodies of the invention, these may be grown in vitro or in a body cavity of an animal. The antibody-producing cell is injected into an animal such as a mouse resulting in the formation of an ascites tumour which releases high concentrations of the antibody in the ascites of the animal. Although the animals will also produce normal antibodies, these will only amount to a minor percentage of the monoclonal antibodies which may be purified from ascites by standard purification procedures such as centrifugation, filtration, precipitation, chromatography or a combination thereof.

An example of a suitable manner in which the monoclonal antibody may be produced is as a result of fusing spleen cells from immunized mice (such as Balb/c mice) with myeloma cells using conventional techniques (e.g. as described by R. Dalchau, J. Kirkley, J. W. Fabre, "Monoclonal antibody to a human leukocyte-specific membrane glycoprotein probably homologous to the leukocyte-common (L-C) antigen of the rat", *Eur. J. Immunol.* 10, 1980, pp. 737–744). The fusions obtained are screened by conventional techniques such as binding assays employing compounds comprising antigen or epitope of the invention or an anti-idiotypic antibody as described above isolated by the above-described methods.

As mentioned above, the interferon proteins according to the invention possess a number of properties which make them valuable as therapeutic or prophylactic agents, including antiviral activity, antitumour activity and immune system modulating activity. These activities make them useful generally as antiviral and antitumour agents and agents modulating the activity of the immune system. However, the fact that the new interferons are produced by the human trophoblasts, that is, cells present in a very specialized environment, with their very specialized functions, make these interferon proteins especially valuable in connection with treatment of adverse conditions in connection with pregnancy or labour, such as indicated above.

In accordance with this, one aspect of the invention relates to a method for inhibiting tumoral growth or metastatic processes in a warm-blooded animal such as a human, comprising administering an effective amount of an interferon according to the invention or a mixture of such interferons to an animal. In particular, the interferon is an α-interferon, or a mixture of an α- and a γ-interferon, according to the invention, but in accordance with what is stated above, also mixtures of α-interferons according to the invention and mixtures of one or more α-interferons according to the invention together with other interferons according to the invention are of interest in this connection.

Another aspect of the invention is a method for preventing graft-versus-host reaction in a warm-blooded animal such as a human, comprising administering an effective amount of an interferon according to the invention or a mixture of such interferons to the animal. The preferred interferon for this purpose is α-interferon and β-interferon according to the invention.

Another aspect of the invention is a method for prolongating an allograft survival in a warm-blooded animal such as a human, comprising administering an effective amount of an interferon according to the invention to the animal. In this case, α-interferon and β-interferon protein according to the invention will often be preferred.

A further aspect of the invention is a method for treating leukemia, such as hairy cell leukemia or chronic myeloid leukemia, in a warm-blooded animal such as a human, comprising administering an effective amount of an interferon according to the invention, in particular an α-interferon, or a mixture and α- and a γ-interferon of the invention to the animal. The amount of the interferon administered is typically about 1000 million units over a year.

A further aspect of the invention relates to a method for treating myelomatosis in a warm-blooded animal such as a human, comprising administering an effective amount of an interferon according to the invention, in particular an α-interferon according to the invention, or a β-protein according to the invention, or a mixture of α- and γ-interferons according to the invention, to the animal. Also in this case, the amount of interferon administered is suitably about 1000 million units over a year.

A still further aspect of the invention is a method for inhibiting, controlling or preventing viral activity in a warm-blooded animal such as a human, comprising administering to the animal an effective amount of an interferon protein as defined in claim 1 or a mixture of such interferon proteins. The viral activity may, e.g., be retroviral activity, such as HIV activity, or it may be hepatitis activity or herpes simplex virus activity. For this purpose, α- or β-interferon according to the invention, or mixtures of interferons according to the invention comprising γ-interferons according to the invention, will normally be preferred.

In accordance with what is stated above, this method is particularly valuable when used for preventing virus from a human mother infected with the virus from infecting her noninfected fetus during pregnancy or during labour. The administration may suitably be performed by injection into the amniotic fluid.

For these antiviral purposes, the interferon protein is suitably an α- or a β-interferon according to the invention as characterized under d) above, administered, e.g., in an amount of about $5 \times 10^6$ units 3 times a week by intravenous injection or by injection into the amniotic fluid.

Another important aspect of the invention is a method for treating infections selected from virus infections and non-virus infections in a warm-blooded animal such as a human in cases where acute systemic maternal infections are diagnosed, comprising administering to the animal an effective amount of an interferon protein as defined in above or a mixture of such interferon proteins. Also in this case, the administration is suitably performed by intravenous injection or injection into the amniotic fluid. The interferon protein is preferably an α- or a β-interferon as described above in a dose of 100,000 to 1,000,000 units per injection.

A further aspect of the invention is a method for treating malignant tumours (choriocarcinomas) arising from the placenta in a warm-blooded animal such as a human, comprising administering to the animal an effective amount of an interferon protein according to the invention. Again, the administration is suitably performed by injection into the amniotic fluid. The interferon protein is suitably a mixture of α-interferons according to the invention or a mixture of α- and γ-interferonsor a mixture of β- and γ-interferons according to the invention administered in an amount of about $5 \times 10^6$ units 3 times a week.

For the above purposes, the interferons are suitably used in the form of pharmaceutical compositions comprising an interferon or interferons in association with a stabilizer in a manner known per se. The stabilizer may, e.g., be human albumin.

In addition to being used alone or in admixture with each other, the interferons according to the invention may also be used in admixture with other active compounds, in particular other interferons, depending on the condition to be treated.

THE BRIEF DESCRIPTION OF THE DRAWINGS

FIG. 1. HP-DLAC of crude trophoblast interferon on HEMA-BIO 1000 VS 3GA. Interferon ($2.05 \times 10^6$ IU) was applied to a column and interferon activity (□) was eluted with a 60 min linear gradient of 0.2M- to 1.0M-NaCl (---) for 60 min. The column was further eluted with increasing concentrations of ethylene glycol (---) from 0 to 50% for 10 min and 50% for 35 min. The $A_{280}$ is shown by the continuous line.

Figure 2A:
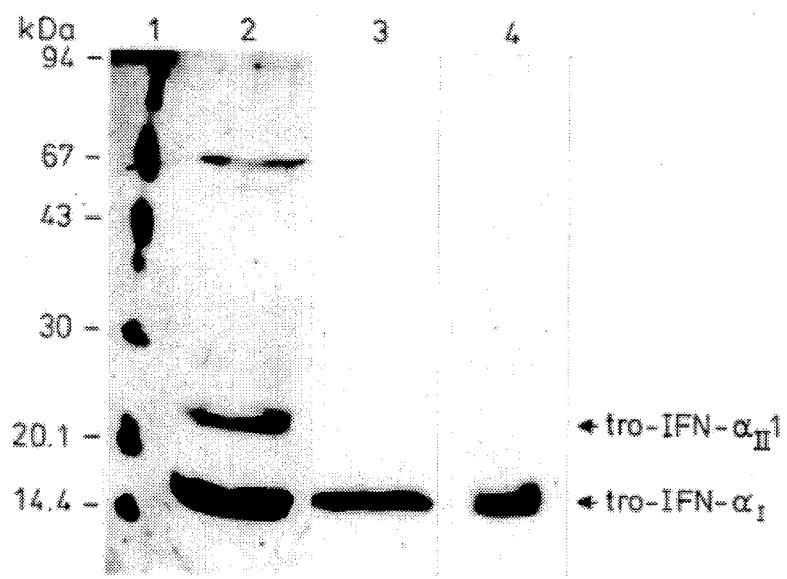
Figure 2B:
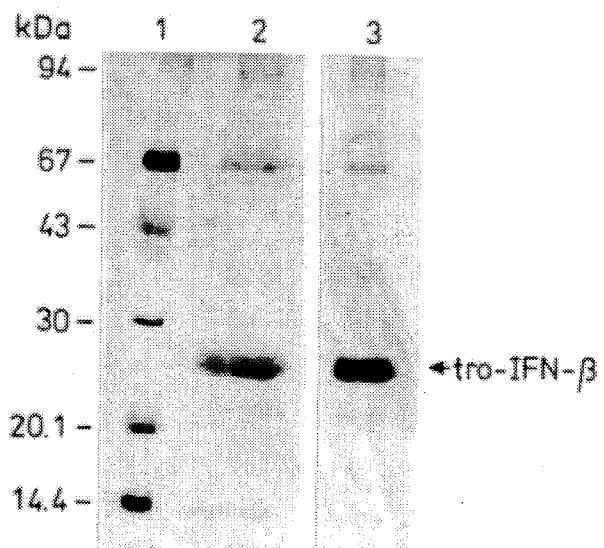

FIGS. 2A–2B. Silver-stained SDS-PAGE containing purified trophoblast interferons. (FIG. 2A) Lane 1, standard protein markers; lane 2, trophoblast $\alpha_I$-interferon and trophoblast $\alpha_{II}$1-interferon purified from a crude trophoblast interferon preparation on a HEMA-BIO 1000 VS-anti-α-interferon antibody column; lanes 3 and 4, HP-IAC-purified trophoblast $\alpha_I$-interferon under reducing and non-reducing conditions respectively. (FIG. 2B) Lane 1, standard protein markers; lanes 2 and 3, HP-DLAC-purified trophoblast β-interferon (from fraction 56 to 58 in FIG. 1) under reducing and non-reducing conditions respectively.

FIGS. 3A–3C. Con A affinity chromatography of the trophoblast interferons. Trophoblast β-interferon and trophoblast $\alpha_I$- and $\alpha_{II}$-interferons were purified using tandem HPAC (high performance affinity chromatography) and the resulting fractions were injected separately onto HEMA 1000 VS-Con A column (50 mm×4.6 mm I.D). After washing the column with column buffer (20 mM sodium phosphate buffer, pH 7.2, containing 1M NaCl and $MnCl_2$, $CaCl_2$ and $MgCl_2$) the bound interferon having interferon activity were eluted with 0.1 M α-methyl-D-mannopyranoside and 50% ethylene glycol (↓) in the column buffer (FIG. 3A) and (FIG. 3B). Trophoblast $\alpha_I$-interferon did not bind to the column but was eluted in the flow-through fractions (FIG. 3C).

Figure 4:
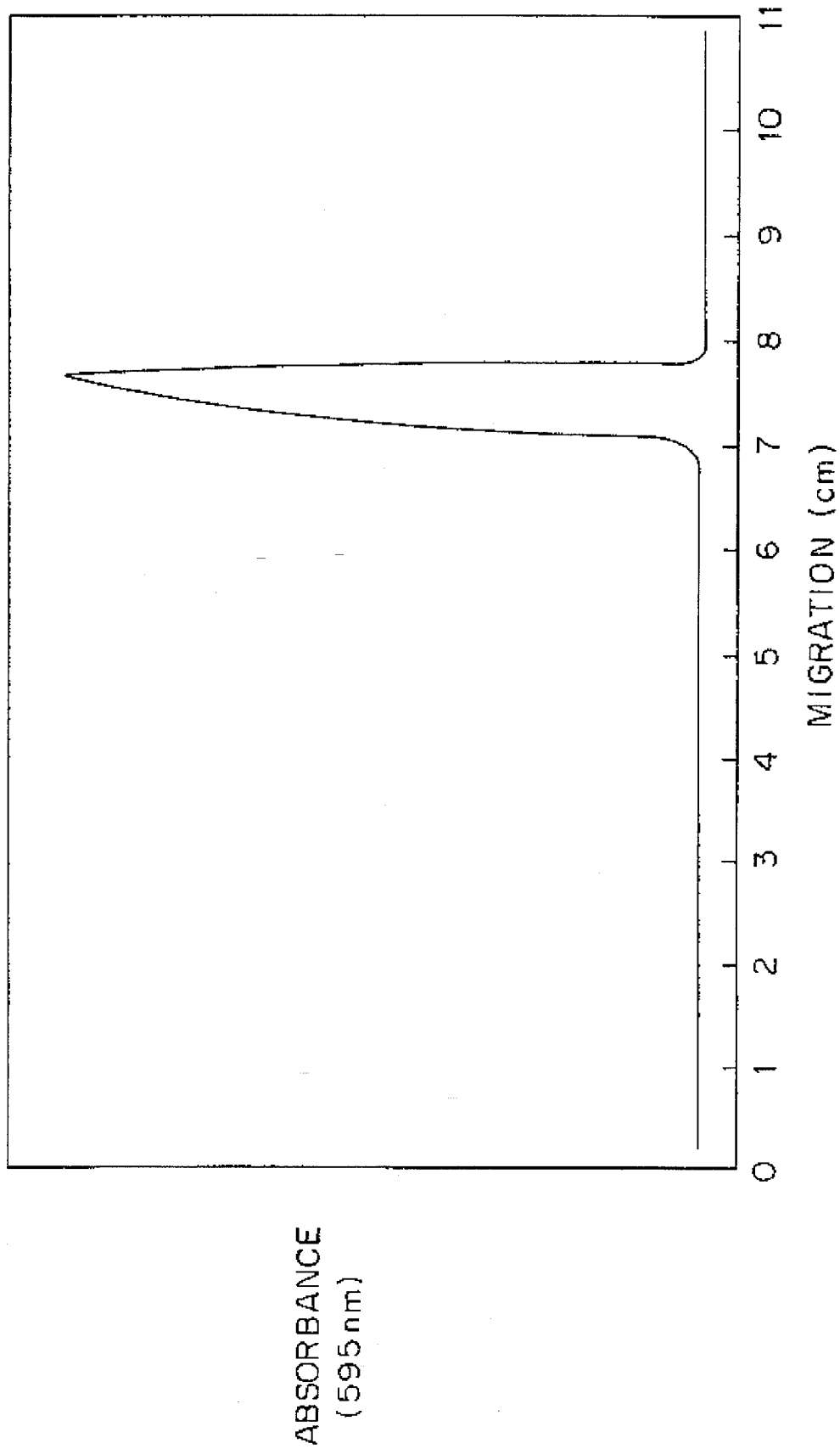

FIG. 4. Densitometric analysis of Coomassie-stained SDS gel of the purified trohoplast β-interferon preparation, The scanning analysis showed the purity to be greater than 99%.

Figure 5:
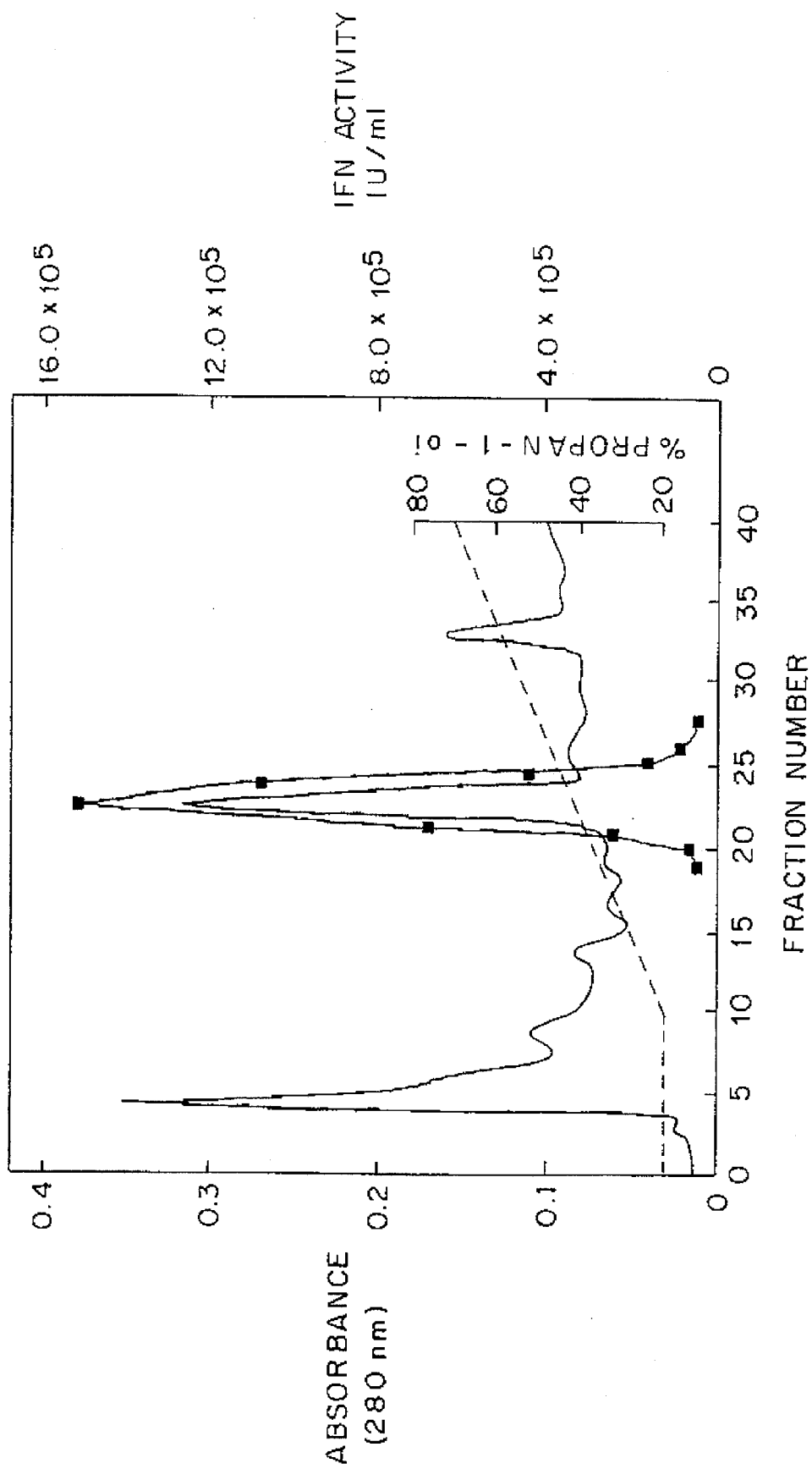

FIG. 5. RP-HPLC of HP-DLAC-purified trophoblast β-interferon on Separon SGX c-18.25 ml of interferon sample, containing $1.47 \times 10^6$ IU, was applied to a column (3 mm×150 mm) equilibrated with 20% propan-1-ol in mobile phase A (pyridine/acetic acid pH 5.0). Bound proteins were eluted with a linear gradient (---) of 20–70% propan-1-ol in Buffer A. Interferon activity (□) was eluted between 40 and 43% propan-1-ol.

Figure 6:
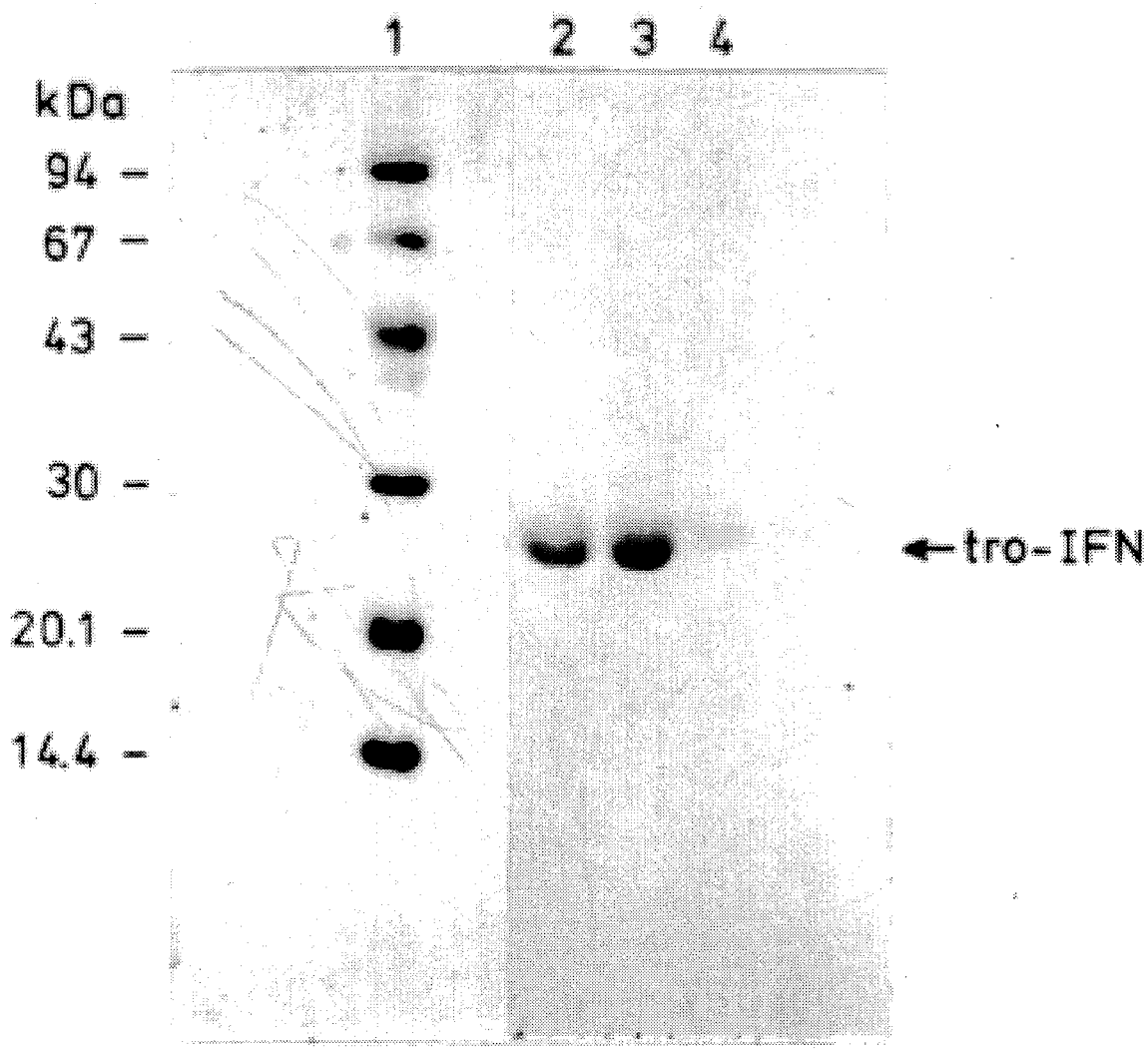

FIG. 6. SDS-PAGE of the RP-HPLC-purified trophoblast β-interferon. Lane 1 is standard molecular mass markers. Lanes 2–4 are pooled fractions 22–24 (see FIG. 5) with the highest interferon antiviral activity.

FIG. 7. The structure of HEMA-BIO 1000 VS 3GA-Cibachron Blue 3GA (A) was attached via spacer arm, 1,2-diaminobutane (B) to HEMA-BIO (D) activated with divinyl sulphone (C).

EXAMPLE 1

Isolation of Human Placental Trophoblast Cells, Establishment of a Trophoblast Cell Culture and Induction of Interferon Production Isolation and purification of human placental trophoblast cells and establishment of a trophoblast cell culture Human placental trophoblast cells from term placenta were isolated as follows.

1) Biopsies were taken from the placenta after removing the shell-site.
2) The tissue was placed in a container with PBS containing Fungizone®, penicillium and streptomycin. (fungizone-B 10.000 μg/ml, amphofericin-B 250 μg/ml, penicillium 10.000 IU/ml and streptomycin 10.000 μg/ml was added to 500 ml s-PBS (sterile PBS)).
3) The biopsies were cut into 1×1×1 cm pieces.
4) The tissue was transferred to another container and s-PBS was added. After sedimentation of the tissue, the tissue was washed repeatedly with s-PBS until the supernatant was clear.
5) Thereafter, the tissue was filtered through a double layer of gauze.
6) The thereby obtained tissue was transferred to a new container with 300 ml trypsinization liquid with a temperature of 37° C. The trypsinization liquid was prepared by adding 1.125 g of trypsin to 900 ml PBS containing 5 mM $Mg^{++}$ and adjusting the pH to 7.4 followed by sterilization. 300 μl DNAse was added per 300 ml detrypsinating liquid.
7) After 30 min at 37° C. under rotation, all was filtered through a double layer of gauze and the tissue was transferred to another round of 30 min of trypsinization, The supernatant was discarded.
8) The sample was filtration through a double layer of gauze into 10 ml fetal calf serum whereby the trypsin was inactivated. The retained tissue was taken through another round of trypsinization for 30 minutes.
9) The supernatant was removed and the cells resuspended in 2×40–50 ml of s-PBS, The cell suspension was centrifugated 300 g for 7 minutes.
10) All was filtered through two layers of gauge into 10 ml fetal calf serum. The retained tissue was discarded.
11) The supernatant was centrifugated 300 g for 7 min.
12) The supernatant was removed and the cells resuspended in 25–35 ml of PBS and filtered through a six-layer of gauze and then was centrifugated at 300 g for 7 min.
13) The cells were placed on a Percoll gradient by suspending the cells in 10 ml 70% Percoll which was applied underneath 20 ml 25% Percoll. Finally, 10 ml s-PBS was applied and the resulting gradient was centrifugated for 20 min at 800 g at 4° C.
14) The mononuclear cells were collected from the gradient, resuspended in PBS and centrifugated at 300 g for 7 min.
15) The supernatant was removed, the cells resuspended in PBS and centrifugated again at 300 for 7 min.
16) The supernatant was removed, the cells were resuspended in a known amount of PBS and counted.
17) The cells were centrifugated and resuspended in with 30% non heat inactivated fetal calf serum. In 925 μl of RPMI containing the cells 75 μl DMSO was added and the cells were stored in frozen condition.

First trimester trophoblast cells from a provoked vaginal delivery were isolated as described in Example 4.

The cells from the term placenta isolated as described above were purified by immunomagnetic microspheres as described by Douglas & King (1989). The purification was performed as follows.

1) After thawing in RPMI, the cells were centrifugated at 300 g for 7 min.
2) The supernatant was removed and the cells resuspended in RPMI at a concentration of $20 \times 10^6$ cells/ml,
3) 20 µl of HLA-abc antibody was added per ml cell suspension.
4) The cells were incubated on ice under gentle rotation for 30 min followed by ×3 washing in RPMI.
5) The cells were centrifugated at 300 g for 7 min and resuspended in RPMI to a concentration of $20 \times 10^6$ cell/ml.
6) The following Dynabeads (Douglas & King, 1989) were added:
   50% CK1 pos.cells: 150 µl Dynabeads M-450 (sheep anti-mouse IgG)/ml suspension.
   70% CK1 pos.cells: 100 µl Dynabeads M-450 (sheep anti-mouse IgG)/ml suspension.
   90% CK1 pos.cells: 50 µl Dynabeads M-450 (sheep anti-mouse IgG)/ml suspension.
9) The cells were incubated for 30 min on ice and gently hand-shaken from time to time.
10) The cell suspension was then placed on a magnetic plate. The cells were left for a few minutes and the supernatant was removed. The Dynabeads were washed with PBS and placed on the magnetic plate again for removal of the remaining Dynabeads.
11) PBS was added and the sample was centrifugated at 300 g for 7 min. The cells were resuspended and counted.
12) The cells were examined for the presence of CK-1, M 717 and M 821, HLA-abc, M 736, vimentin M 877 and M 725, macrophage M 718 (Dakopatts A/S, Denmark) by indirect fluorescence. The secondary rabbit to mouse FITC labelled antibody F 313 of F 201 from Dakopatts.
13) The trophoblast cell culture was established by seeding the trophoblast cells at a density of $1 \times 10^6$ cells/ml in RPMI-1640 supplemented with 10% FCS.

Production of Interferon

In order to induce a production of interferon, stimulation of the cells was needed.

The cells were cultured for 24 h, at 37° C. and 5% $CO_2$ in air RPMI-1640 suplemented with 10% fetal calf serum. The induction of the interferon performed either by infecting the cells with Sendai virus or by using polyriboinosinic-polyribocytidylic acid (poly(rI)-poly(rC)). When using Sendai virus as inducer of the interferon, the cells were infected with Sendai virus using 200 HAU/$10^6$ cells for 1 h in serum-free RPMI-1640. Unadsorbed virus was removed by washing the cells twice with serumfree medium. When using polyriboinosinic-polyribocytidylic acid (poly(rI)-poly(rC)) (Sigma Chemical Company, St. Louis, Mo., USA), the cells were incubated with 10 µg/ml for 1 hour and the culture was washed three times with serum-free medium and then further cultured with RPMI 1640+5% fetal calf serum.

Culture supernatants were harvested 18 h after induction. Virus-stimulated supernatants were acidified to pH 2.0 using hydrochloric acid for 48 h at 4° C. and then neutralized to pH 7.2. The crude interferon was precipitated by adding 1 g ammonium sulphate per 2 ml of interferon preparation. The precipitate was redissolved in 0.02-M sodium phosphate buffer pH 7.2 and dialyzed against two changes of 500-fold excess of the same buffer for 10 h at 4° C.

EXAMPLE 2

Purification of the Various Types of Interferon and Further Examination of the Purified Interferon Preparation of the Columns Used in the Chromatographic Procedures The HEMA-BIO 1000 VS 3GA adsorbent (HEMA-BIO 1000 VS=2-hydroxyethyl methacrylate vinyl sulphone with an exclusion limit at molecular weight 1000), synthesized as described below, is a unique adsorbent for interferon purification. It does not swell in water. It is rigid and therefore can tolerate the high mobile phase flow rates typical of HPLC. As appears from the following, it results in a very high degree of purification.

Synthesis of HEMA-BIO 1000 VS 3GA

HEMA-BIO 1000 VS 3GA (see FIG. 7) was prepared by covalently attaching Cibacron Blue 3GA (Sigma Chemical Company, St. Louis, Mo., USA) via a spacer arm, 1,4-diaminobutane, to vinyl sulphonate-activated HEMA-BIO 1000 (10 µm particle size, Tessek A/S, Denmark). 6 g of dry HEMA-BIO 1000 VS (10 µm) was suspended in 25 ml of 0.1M $NaHCO_3$—$Na_2CO_3$ buffer pH 11.5 for 10 min and 1,4-diaminobutane was added to a final concentration of 0.5M. The mixture was incubated overnight at room temperature by rotation on a Rotamix (HETO, Birkerød, Denmark). The gel was settled by centrifugation and extensively washed with water (500 ml). The gel was then suspended in 30 ml of 0.1 M $NaHCO_3$—$Na_2CO_3$ buffer pH 9.0 containing Cibacron Blue 3GA (600 mg, 0.775 mmol). The mixture was incubated overnight at room temperature by rotation on a Rotamix. After incubation, the gel was settled by centrifugation and the supernatant was removed. The HEMA-BIO 1000 VS 3GA was washed with water (500 ml), 1.5M NaCl (300 ml) and 0.02M sodium phosphate buffer pH 7.2 (500 ml). The gel was then packed in a biocompatible PEEK (Poly Ether Ether Ketone) column (7.5 mm×250 mm, Tessek A/S, Aarhus, Denmark) by the upward slurry packing technique under pressure (6 MPa). The concentration of the Cibacron Blue 3GA immobilized on the HEMA-BIO 1000 VS 3GA was determined by spectrophotometric analysis of alkaline hydrolysates as described by Lowry et al (1951). The binding capacity was determined by frontal analysis with human serum albumin in 0.02M sodium phosphate buffer pH 7.2. Thus, continuous injections of human serum albumin were applied to a PEEK column (4.6 mm×50 mm packed with HEMA-BIO 1000 VS 3GA) until protein activity was observed in the eluent. The column was washed and the bound protein was eluted with 2M NaCl in the same buffer. The concentration of the eluted protein was then assayed.

Synthesis of HEMA-BIO 1000 VS - Antibody Column

Immunoadsorbents (such as anti-α-interferon antibodies and anti-β-interferon antibodies) and Concanavalin A (Con A) columns were prepared by adsorption-promoted enhanced covalent immobilization of the antibodies and Con A on macroporous HEMA-BIO 1000 VS.

0.5 g of dry HEMA-BIO 1000 VS was swollen with immobilization buffer (0.1-M sodium borate/0.75M ammonium sulphate buffer pH 8.0) and 5 mg antibodies or 10 mg of Con A (Sigma Chemical Company, St. Louis, Mo., USA) dissolved in 4 ml or 15 ml (for Con A) of immobilization buffer was added to the wetted gels. The immobilization was allowed to proceed under gentle rotation for 16 to 20 h at 4° C., The gels were then settled by centrifugation, the supernatants were removed, the gels were washed eight times with distilled water and residual reactive groups were blocked by incubation with 3 ml of 0.1-M ethanolamine in 0.1-M sodium borate buffer pH 9.0 for 6 h. The gels were then packed in biocompatible PEEK hardware (50 mm×4.6 mm internal diameter).

Chromatographic Procedures

High-performance Dye-Ligand Affinity Chromatography (HP-DLAC)

Concentrated crude trophoblast interferon ($2.05 \times 10^6$ IU) was filtered through 0.22 μm Millipore filter and applied to HEMA-BIO 1000 VS 3GA column (250 mm×7.5 mm I.D.) equilibrated with column buffer (0.02-M sodium phosphate buffer pH 7.2). After the column has been washed with the same buffer containing 0.2-M NaCl, proteins were eluted with a linear gradient of 0.2 to 1.0-M NaCl in 35 min at a flow rate of 1.5 ml/min. The elution from the column was monitored continuously at UV absorbance of 280 nm. The column was further washed with 1.0-M NaCl in the column buffer for 20 min until the absorbance was almost zero. Protein was then eluted from the column by increasing concentration of ethylene glycol in 0.02-M sodium phosphate buffer pH 7.2 containing 1.0-M NaCl; elution was with 0 to 50% for 10 min and 50% for 35 min at a flow rate of 1.5 ml/min. Fractions of 1.5 ml were collected and assayed for interferon antiviral activity.

High-performance Immunoaffinity Chromatography (HP-IAC)

Crude trophoblast interferon preparations and the fractions containing interferon antiviral activity from the HEMA-BIO 1000 VS 3GA column were applied separately to HEMA-BIO 1000 VS-anti-α-interferon (polyclonal) antibody or anti-β-interferon antibody columns. In all cases, the columns were washed 10 min with PBS (phosphate buffer saline) pH 7.4 and proteins were eluted with 0.1-M glycine-HCl pH 2.4. Fractions of 0.5 ml were collected and dialyzed against PBS buffer for 16 h at 4° C. to restore the pH to neutral, and then were assayed for interferon antiviral activity.

Reversed-Phase High Performance Liquid Chromatography (RP-HPCL)

The Interferon containing fractions from the HP-DLAC step were pooled together and dialysed against 0.02M sodium phosphate buffer, pH 7.2, containing 30% glycerol for 1 h to remove ethylene glycol and also to concentrate the sample. The dialysed sample was applied to Separon SGX C-18 column (CGC glass cartridge of 3 mm×150 mm, with a metal column holder) that has previously been equilibrated with a mobile phase consisting of 80% Solvent A (1M pyridins/acetic acid pH 5.0) and 20% Solvent B (100% propan-1-ol). The column was washed for 20 min with the same mobile phase, followed by elution of interferon activity with a linear gradient from 20 to 70% Solvent B in Solvent A. The gradient elution was carried out in 60 min at a flow rate of 0.25 ml/min. Elution from the column was monitored continually at UV absorbance of 280 nm (0.32 absorbance units full-scale) and fractions of 0.5 ml were collected and then were assayed for interferon activity.

Purification of the Trophoblast Interferons

FIG. 1 illustrates the HP-DLAC of crude trophoblast interferon on HEMA-BIO 1000 VS 3GA. The trophoblast interferons bound completely when applied in 0.02M sodium phosphate buffer pH 7.2 at low ionic strength (0.2M NaCl). Development of the column with a linear concentration gradient of sodium chloride separated 20% of the total interferon activity applied into five peaks (fractions 21 to 40 eluted at 0.6 to 0.8M NaCl).

Further development of the column with a linear concentration gradient of the hydrophobic solute ethylene glycol produced two interferon peaks (fractions 50 to 53 and 54 to 70), eluted from the column at ethylene glycol concentrations of 40 to 50% and 50%. A summary of the HP-DLAC of the trophoblast interferons is presented below in Table 1.

TABLE 1

Purification of placental trophoblast interferons (IFN) by HP-DLAC

| | Total activity by (IU × $10^{-4}$) | Total protein (mg) | Specific activity (IU/mg × $10^{-3}$) | Purification (-fold) | Recovery (%) |
|---|---|---|---|---|---|
| Crude tro-IFN | 205 | 401.9 | 5.10 | 1 | 100 |
| Fractions 21–40 | 41 | 0.328 | 1250 | 245.0 | 20 |
| Fractions 50–53 | 742 | 0.070 | 1060 | 207.8 | 3.6 |
| Fractions 54–70 | 138 | 0.076 | 18200 | 3568.6 | 67.32 |

TABLE 2

Summary of a two-dimensional purification of trophoblast β-interferon.

| Step | Total IFN activity | Total protein (mg) | Spec. activity | Purification fold | Recovery (%)[a] |
|---|---|---|---|---|---|
| Cult. supern. | $2.04 \times 10^6$ ($1.53 \times 10^6$)[b] | 346.9 | $5.88 \times 10^3$ | 1 | 100 |
| HP-DLAC | $1.47 \times 10^6$ | 0.108 | $1.36 \times 10^7$ | 2312.9 | 96 |
| RP-HPLC | $1.24 \times 10^6$ | 0.012 | $1.03 \times 10^8$ | 17517 | 81(61)[c] |

[a] % Recovery over the total β-interferon activity in the crude preparation
[b] Total β-interferon activity in the crude preparation
[c] Recovery of trophoblast β-interferon over the total interferon activity.

Further purification in the form of rechromatography of the HP-DLAC-purified trophoblast β-interferon by RP-HPLC on Separon SGX C-18 is shown in Table 2 above. As appears from the table, the rechromatography resulted in a purification of β-interferon having a specific activity of $1.03 \times 10^8$ IU/mg of protein with a 17,517-fold purification over the crude preparation. The chromatogram is shown in FIG. 5.

Determination of the Protein Concentration

The concentration of protein in crude trophoblast interferon preparations was determined by the dye binding assay (Bradford, 1976) using bovine serum albumin as a standard. The concentration of purified interferon was measured by absorbance at 280 nm, or derivatization with fluorescamine and injecting the samples into a fluorescence HPLC monitor and using known concentrations of BSA as a standard.

Polyacrylamide Gel Electrophoresis

Slab SDS-PAGE was carried out according to Laemmli (1970) using a voltage of 200 V and running the SDS-PAGE for 45 min or until the sample is 1 cm from the bottom. Freeze dried interferon samples were prepared with 5% 2-mercaptoethanol or without 2-mercaptoethanol. The following amounts of the various interferons were used in order to determine the size of the various interferon molecules: 40.000 IU of β-interferon, 45.000 IU of $\alpha_I$-interferon, 45.000 IU of $\alpha_{II}$-interferon, After electrophoresis, the gels were silver stained using Bio-rad silver staining kit (Catalogue number 161-0443) and scanned on Biomed SLR 1 D/2D scanner (Biomed Instruments Inc. California, USA) to determine the molecular mass by comparison with Bio-Rad standard protein standards. To determine the interferon antiviral activity on unstained gels, 2-mm slides of the gel were extracted at 4°

C. for 24 h into 0.5 ml volumes of PBS buffer pH 7.4 containing 0.1% SDS and 0.02% $NaN_3$. Aliquots (100 µl) were then taken and assayed for interferon antiviral activity.

FIGS. 2A and 2B show the patterns obtained by SDS-PAGE on fractions from HP-IAC performed on crude trophoblast interferon preparation and the patterns obtained by SDS-PAGE on HP-DLAC-purified trophoblast $\alpha_I$-interferon (fractions 21 to 40 from FIG. 1) on a HEMA-BIO 1000 VS-anti-α-interferon (polyclonal) antibody column. Antiviral activity neutralization assays of interferons extracted from unstained gels (similar to the gel in FIG. 2A under reducing and non-reducing conditions, showed that trophoblast $\alpha_I$-interferon and trophoblast $\alpha_{II}1$-interferon activities corresponded to the protein bands with molecular masses of 16 and 22 kDa respectively; No interferon activity was associated with the 67 kDa protein band. FIG. 2(b) shows the SDS-PAGE of trophoblast β-interferon (from fractions 56 to 58 in FIG. 1); trophoblast β-interferon migrated as a 24-kDa protein on reducing and non-reducing SDS-PAGE (FIG. 2B) lanes 2 and 3 respectively).

The antiviral activity of the crude trophoblast interferon preparation and the purified interferon were stable after 24 h incubation at pH 2 in 0.1-M glycine.

EXAMPLE 3

Examination of the Interferon Produced by the Trophoblast Cells

Glycoprotein Analysis

The presence of sugar residues in the trophoblast interferons was determined by their binding to Con A affinity chromatography on HEMA 1000 VS-Con A.

After injection of the interferon samples, the column was washed with column buffer (20 mM sodium phosphate buffer pH 7.2, containing 1M NaCl and $MnCl_2$, $CaCl_2$, and $MgCl_2$). Bound interferons were then eluted with 0.1M α-methyl-D-mannopyranoside and 50% ethylene glycol in the column buffer.

Trophoblast $\alpha_{II}$-interferon and trophoblast β-interferon did bind to Con A affinity column (se FIGS. 3A–3C), whereas trophoblast $\alpha_I$-interferon did not bind. This suggests that trophoblast $\alpha_{II}$-interferon and trophoblast β-interferon are glycoproteins whereas $\alpha_I$-interferon may not be a glycoprotein.

Examination of a Cytotoxic Compound Secreted by Trophoblasts After Induction With Virus When determining the biological activity of fractions 55–70 in FIG. 1, it was found that apart from antiviral activity, the interferon purified had cytotoxic effect. At first, it was believed that the impurity was responsible for the cytotoxic effect. Therefore, the material was further purified on an anti-β-interferon column. The cytotoxic compound did not bind to the column. Even in dilutions up to 1,000,000, the eluate showed cytotoxic activity.

In the following, the investigation is made of the cytotoxicity of this compound, prepared by pooling the above-mentioned fractions 55–70, subjecting them to the High performance dye ligand chromatography, and subjecting the eluate from this chromatography to High performance immunoaffinity chromatography on the anti-β-interferon column (whereby the β-interferon is very efficiently bound by the HEMA-BIO 1000 VS 3GA, while the cytotoxic compound passes through the column).

To determine the cytotoxic drug response of the compound in question, two different target cell lines, L-929 and K-562 were used in a tetrazolium dye reduction assay (MTT assay). (P.R. Twentyman, Modification of cytotoxic drug resistance by non-immuno-suppressive cyclosporins. British Journal of Cancer 1988, 57, pp. 254–258). In brief, the target cells L-929 and K-562 where grown in RPMI 10% at 37° C. in 96-well microwells in 100 µl, 20000 cells/well. On day 0 the trophoblast compound was added to the well to obtain different dilutions: 1:10, 1:1000, 1:10000, 1:100000, 1:1000000. After 2 days of cultivation in 5% $CO_2$, 100 µl of medium were added to each well. After 4 days of cultivation 20 µl MTT solution were added to all wells and incubated for further 4 hours. The plates were centrifuged 1 minute at 300 rpm in order to pellet the cells. 150 ml were harvested from each well and 100 µl isopropanol were added. After 5 minutes allowing the crystals to dissolve, the plates were grown on an ELISA reader using an optical density of 570 nm. Control cultures were grown in medium alone. It was found that the cells were killed by the compound in all of the dilutions mentioned.

Examination of the Purity of the Interferons

The purity of the β-interferons purified as described in Example 2 above using HP-DLAC and RP-HPLC purification was determined by densitometric analysis of Coomassie SDS-polyacrylamide gel (see FIG. 6) using Biomed SLR-1D/2D densitometer (Biomed Instruments Inc., California, 92621)

In FIG. 4 is shown the densitometric analysis of the purity of β-interferon. As appears from the figure, a single peak was obtained, showing that a purity of more than 99% was obtained.

Examination of the Antiviral Activity of the Trophoblast Interferons

The antiviral activity of the various interferon preparations was determined by assaying the capability of the sample to inhibit plaque formation in human amniotic cell line WISH (American Type Cell culture, ATCC) by vesicular stomatitis virus (VSV), Indiana strain.

The cells were seeded in 96-well mioroplates (40,000 cells/well). Interferon preparations were titrated by adding 100-µl of two- or four-fold serial dilutions to each well. After incubation for 24 h at 37° C. and 5% $CO_2$ in air, the cells were infected with VSV (50 plaque-forming units per well). The titrations were scored microscopically 24 h after virus inoculation. The highest dilution giving 50% reduction of the viral plaques was considered as the end point.

The interferon titers were standardized by comparison with the National Institute of Health Standard for human α-interferon G-023-902-530) and β-interferon,(G-023-902-527). Also, interferon titers, using human trisomic 21 fibroblast cell lines GM 2504 and GM 2767 (Cell Repository, Camden, N.J., U.S.A) and bovine (MDBK) cells (ATCC) were performed similarly using vesicular stomatitis virus as the challenge; results were expressed as the highest dilution giving 50% protection and the activity expressed as the dilution factor in units/ml.

Antigenic Characterization of the Interferons Using Antibody Neutralizing Test

The antigenic specificities of the crude and isolated trophoblast interferons were determined by antibody neutralization tests, Polyclonal anti-human-α-interferon, anti-human-β-interferon, anti-γ-interferon and anti-human recombinant $\alpha_{II}1$-interferon antibodies were used for the assay and for the preparation of the HPLC sorbents.

Polyclonal anti-α-interferon was obtained from Boehringer Mannheim (produced in Balb/c mice using human α-interferon purified from Sendai virus-stimulated human lymphoblastoid cells) and neutralize human α-interferon and recombinant $α_I$-interferon and $α_{II}$-interferon but do not react with anti-β-interferon or anti-γ-interferon.

Polyclonal human anti-βinterferon antibodies, produced in horses immunized with human β-interferon (fibroblast), was obtained form Boehringer Mannheim (Germany) and do not react with human $α_I$-interferon, $α_{II}$-interferon, or γ-interferon.

Anti-recombinant $α_{II}1$-interferon antibodies were supplied by Günther R. Adolf (Dept. of Biotechnology, Dr. Boehringer-Gasse, A-1 121 Vienna, Austria) and do not react with $α_I$-, β- or γ-interferon.

Serial dilutions of interferon and a fixed dilution of antibody in 10-fold excess were incubated for 1 h at 37° C. and residual antiviral activity was determined as described above in "Examination of the antiviral activity of the trophoblast interferons".

Antiviral Specificity of Trophoblast Interferons on Different Types of Cells

In Table 3 is shown the antiviral activities of the trophoblast interferons on different human and bovine cell lines.

TABLE 3

Protection of cell lines from different species against VSV infection by trophoblast interferon (IFN)

| | | Antiviral activity* | | |
|---|---|---|---|---|
| Species | Cell line | tro-IFN-$α_I$ | tro-IFN-$α_{II}1$ | tro-IFN-β |
| Human | WISH | 64 | 64 | 256 |
| Human | GM 2504 | 192 | 224 | 768 |
| Human | GM 2767 | 192 | 224 | 768 |
| Bovine | MDBK | 128 | 256 | 2 |

*Antiviral activity is expressed as the highest dilution giving 50% protection against VSV.

As appears from Table 3, the trophoblast interferons exhibited a broad spectrum of antiviral activities on the human cells (WISH (American Type Cell Culture), GM 2504 and GM 2767 (both trisomy 21 fibroblasts, Cell Repository, Cambden, N.J., U.S.A.) tested, but trophoblast $α_I$-interferon and $α_{II}$-interferon protected bovine cell lines better than human cells (two fold and four fold, respectively, relative to human WISH cells). More interestingly, the protection of MBDK cells by trophoblast $α_{II}$-interferon was twice that conferred by trophoblast $α_I$-interferon. In contrast, trophoblast β-interferon did not protect bovine MDBK cells but did protect all the human cell lines tested.

Characterization of Trophoblast Interferons

The trophoblast interferons were identified by antiviral neutralization tests as described above using polyclonal antisera to human interferon $α_I$-, β- and γ- and $α_{II}1$-interferon.

TABLE 4

Antibody neutralization of trophoblast interferons (IFN) isolated by HP-DLAC*

| | Residual antiviral activity after incubation with antisera (%) | | |
|---|---|---|---|
| Anti-human IFN sera | Fractions 21–40 | Fractions 50–53 | Fractions 54–70 |
| α | 0 | 40 | 100 |
| β | 100 | 60 | 0 |

TABLE 4-continued

Antibody neutralization of trophoblast interferons (IFN) isolated by HP-DLAC*

| | Residual antiviral activity after incubation with antisera (%) | | |
|---|---|---|---|
| Anti-human IFN sera | Fractions 21–40 | Fractions 50–53 | Fractions 54–70 |
| $α_{II}1$ | 100 | 40 | 100 |
| v | 100 | 100 | 100 |
| α + β | ND☐ | 0 | ND |
| $α_{II}1$ + β | 100 | 0 | ND |
| α + $α_{II}1$ | 0 | 40 | 100 |

*Neutralization tests were performed with a 10-fold excess of the respective antiserum.
☐ND = Not determined.

Polyclonal antiserum to human β-interferon neutralized 75% of the antiviral activity of crude trophoblast interferon samples (initially 800 IU/ml, 200 IU/ml after treatment) whereas the anti-α-interferon neutralized 25% of the activity (initially 800 IU/ml, 600 IU/ml after treatment).

The results appear from Table 4 above. Fractions 21 to 40 (see FIG. 1), eluted from the column by NaCl (0.6 to 0.8-M) were completely neutralized by antiserum to human interferon $α_I$ antibodies, but not by anti-$α_{II}1$-interferon, anti-β-interferon and anti-γ-interferon. This showed that the five interferon peaks were $α_I$-interferon. However, the interferon peak fractions (50 to 53) that were eluted from the column using ethylene glycol concentrations between 40 to 50% were partially neutralized by polyclonal anti-β-interferon antibodies, and to the same extent by anti-α-interferon and anti-$α_{II}1$-interferon antibodies. These interferon fractions were completely neutralized by a combination of anti-$α_{II}1$-interferon and anti-β-interferon antibodies, and polyclonal anti-α-interferon and anti-β-interferon antibodies, but not polyclonal anti-α-interferon and anti-$α_{II}1$-interferon antibodies. This suggests that fractions 50 to 53 were a mixture of trophoblast $α_{II}$-interferon and trophoblast β-interferon.

Fractions 50 to 53 (see FIG. 1) were further characterized by passing through HEMA-BIO 1000 VS-anti-β-interferon (polyclonal) column as described above. The antiviral activity of the flow-through fractions and the bound interferon eluted from the column at pH 2.4 was characterized further using antiserum to human α-interferon, β-interferon and recombinant human $α_{II}1$-interferon as appears from Table 5. These assays showed that the antiviral activity of the flow-through fractions was not neutralized by antiserum to β-interferon but was completely neutralized by anti-$α_{II}1$-interferon and polyclonal anti-α-interferon antisera. However, the bound interferon was completely neutralized by human anti-β-interferon antiserum.

TABLE 5

Neutralization of the antiviral activity of fractions 50 to 53 after passage through an anti-β-interferon antibody column

| | Residual antiviral activity (%) | |
|---|---|---|
| Anti-human IFN serum* | Flowthrough | Bound |
| None | 100 | 100 |
| $α_{II}1$ | 0 | 100 |
| α | 0 | 100 |
| β | 100 | 0 |

*The anti-IFN immune sera were used in 10-fold excess.

Determination of the Thermal Stability of the Antiviral Activity

The thermal stability of β-interferon was determined at a temperature of 37° C. and 56° C. The interferon samples were heated to 37° C. or 56° C. for various times. After heating, samples were allowed to cool to room temperature or were stored on ice for 1 hour until they were assayed for antiviral activity using the method as described above.

It was found that the β-interferon retained 55% of its antiviral activity at 37° C. for 3 hours. However, 50%, 75% and 97% of the antiviral activity was lost after 10 min, 15 min and 60 min respectively at 56° C.

EXAMPLE 4

Production of γ-Interferon by First Trimester Placental Trophoblasts Cell Cultures Isolation of First Trimester Trophoblast First trimester trophoblasts were isolated by a modification of the method of Fisher (1989) from villous tissue as follows.

1) The tissue is transported from the hospital in PBS containing Penicillium/Streptomycin and Fungizone (the same concentration as used for term trophoblast cells).
2) The tissue was sectioned in pieces of 2–3 mm$^2$.
3) The tissue was allowed to sediment and thereafter washed repeatedly with s-PBS until the supernatant was clear. The tissue was centrifugated, collected and centrifugated again for 10 min at 300 g.
4) The tissue was weighed.
5) The tissue was placed in a 100 ml bottle with a detrypsinating liquid consisting of 0.625 g trypsin to 600 ml PBS with 5 mM $Mg^{++}$, pH 7.4, and 200 µl DNA-se (this corresponded to approximately 40 g of tissue).
6) After 35 min at 37° C. with rotation, the thus obtained sample was filtered trough 2 layers of gauze, inactivated with sterile serum and centrifugated at 300 g for 7 min.
7) The tissue was weighed.
8) The tissue was washed and centrifugated at least twice and filtered through 6–8 layers of gauze.
9) The cells were resuspended in 10 ml 70% Percoll which was applied underneath 20 ml 25% Percoll. Finally, 10 ml s-PBS was applied and the resulting gradient was centrifugated for 20 min at 800 g at 4° C. (break off).
10) The bands containing cells (as seen under microscope) were aspirated.
7) The cells were washed in s-PBS and counted. Then, the cells were stored frozen in 30% RPMI and 15% DMSO in approximately 10 millions cells per ampule.
8) Selective detaching of trophoblast cells using EDTA on ice was used to further purify the cells. $10^6$ cells/ml were seeded for 24 h in RPM1 1640 containing 10% fetal calf serum. First trimester trophoblasts were detached from the mixture by adding 0.02% EDTA to the cells after aspiration of the medium. The growth container containing the cells was kept on ice for 10–12 min. Detached trophoblast cells were collected and washed twice with RPMI containing 10% medium and were reseeded at a density of $5 \times 10^5$ cells/ml in the same medium.

Induction of the Production of γ-Interferon

First trimester trophoblasts cells seeded at a density of $5 \times 10^5$/ml and cultured for 24 h in RPMI-1640 supplemented by 10% fetal calf serum. After 24 h, the medium was removed and replaced with RPMI-1640+10% fetal calf serum containing the γ-interferon inducer in the form of 100 U/ml of 1L-2 (interleukin-2) and 5 µg/ml of phytohaemagglutinin (PHA). The cells were cultured for 5 days and 200 µl of medium were collected every day and examined for interferon activity. On the 5th day, the supernatant was collected and centrifuged at 2000 rpm for 20 min at 4° C. and stored at −70° C.

Interferon Bioassay

Examination of antiviral activity of the γ-interferon was performed as described above by assaying the capability of the γ-interferon to inhibit the plaque formation in human amniotic cell line WISH (ATCC) by vesicular stomatitis virus (VSV), Indiana strain. Cells were seeded in 96-well microplates (40,000 cells/well). Interferon preparations were titrated by adding 100-µl of two-fold serial dilutions to each well. After incubation for 24 h at 37° C. and 5% $CO_2$ in air, the cells were infected with VSV (50 plaque-forming units per well). The titrations were scored microscopically 24 h after virus inoculation. The highest dilution giving 50% reduction of the viral plaques were considered as the end point.

Antibody Neutralization of the γ-Interferon Activity

The antibody neutralization assay was performed as described above. Polyclonal rabbit and monoclonal mouse antibodies to human γ-interferon were obtained from Serotec, Oxford, England, and Janssen Biochimica, Belgium respectively. These antibodies do not react with human α-interferon or β-interferon. A single dilution capable of neutralizing 10-times the activity of the test interferon activity was incubated with various concentrations of the trophoblast γ-interferon preparation for 1 h at 37° C. The samples were then assayed for the residual interferon antiviral activity.

In Table 6 below is shown the production of γ-interferon in first trimester trophoblast cell cultures stimulated with 1L-2 and phytohaemagglutinin. As seen from the Table, the γ-interferon production peaked 96 h (4 days) after the induction.

TABLE 6

γ-interferon production in first trimester trophoblast as a function of time

| Time (h) | interferon titre (U/ml) |
|---|---|
| 0 | 0 |
| 24 | 80 |
| 48 | 80 |
| 72 | 160 |
| 96 | 640 |
| 120 | 640 |

Table 7 shows the antiviral activity of γ-interferon as assayed using the neutralization assay and using specific human γ-interferon antibodies. The three interferon preparations, that is samples 1, 2 and 3 had antiviral activities of 640 U/ml, 320 U/ml and 160 U/ml respectively. The antiviral activity of the samples was completely neutralized by anti-human γ-interferon but not anti-human β-interferon or anti-human α-interferon. Therefore, the antiviral activity in the supernatant of the human trimester trophoblast cell culture induced by phytohaemagglutinin and 1L-2 is caused by γ-interferon.

TABLE 7

Trophoblast interferon (IPN) antiviral neutralization test

| IFN samples | Residual antiviral activity (%) after incubation with | | |
|---|---|---|---|
| | anti-human α-IFN | anti-human β-IFN | anti-human γ-IFN |
| tro-IFN (PHA/IL-2) 1 | 100 | 100 | 0 |
| tro-IFN (PRA/IL-2) 2 | 100 | 100 | 0 |
| tro-IFN (PHA/IL-2) 3 | 100 | 100 | 0 |

EXAMPLE 5

Differential Interferon Production in Human First and Third Trimester Trophoblast Cultures Stimulated With Virus Viruses Newcastle Disease virus (NDV, Strain 1B) and Sendai virus (Parainfluenza 1) were obtained from American Type Culture collection (ATCC) and were propagated in the allantoic cavities of 10 day old embryonated eggs by inoculation of a $10_{-2}$ or $10_{-3}$ dilution of infected allantoic fluids. After the eggs were incubated at 35° C. for 3 days, the allantoic fluids were harvested and the infectivity was titrated in chicken erythrocytes.

Isolation of First and Third Trimester Trophoblasts

Third trimester trophoblast cells were isolated by immunomagnetic microspheres as described above in Example 1. First trimester trophoblasts were isolated as described in Example 4.

Induction of Trophoblast Interferons

Trophoblast cells were seeded at a density of $1 \times 10^6$ cells/ml in RPMI-1640 supplemented with 10% fetal calf serum. The cells were cultured for 24 hours, at 37° C. and 5% $CO_2$ in air, and then were infected with NDV (30 HAU/$10^6$ cells) or Sendai virus (200 HAU/$10^6$) for 1 hour in serum-free RPMI 1640. The unadsorbed virus was removed by washing the cells twice with serum-free medium and further culturing in RPMT 1640+5% fetal calf serum. Culture supernatants were harvested 18 hours after induction. Virus-stimulated supernatants were acidified to pH 2.0 for 48 hours at 4° C. and then neutralized to pH 7.2.

Interferon Antiviral and Neutralization Assay

These assays were performed as described previously in Example 3.

RESULTS

Table 8 shows the differential interferon production in first- and third trimester trophoblast cultures stimulated with Sendai and Newcastle Disease viruses. The data demonstrated that first trimester trophoblasts produced higher levels (about 5–7 times) of interferons than third trimester trophoblasts. Furthermore, the interferon compositions varied depending on the inducer used to induce the interferon production. However, the interferon compositions were the same in both cases when induced by the same inducer in the first and third trimester trophoblast cultures.

TABLE 8

Interferon yields and compositions of Sendai- and Newcastle Disease virus-stimulated first and third trimester trophoblast cultures.

| Trophoblast | Inducer virus | IFN yield (IU/$10^6$ cells) | Composition* | |
|---|---|---|---|---|
| | | | IFN α (%) | IFN β (%) |
| First trimester | Sendai | 64000 | 25 | 75 |
| Third trimester | Sendai | 8500 | 25 | 75 |
| First trimester | Newcastle | 80000 | 35 | 65 |
| Third trimester | Newcastle | 16000 | 35 | 65 |

*Determined by interferon antiviral neutralization assay

REFERENCES

ABOAGYE-MATHIESEN, G., TOTH, F. D., JUHL, C., NORSKOV-LAURITSEN, N., PETERSEN, P. M. and EBBESEN, P. (1990). Purification and initial characterization of human placental trophoblast interferon induced by polyriboinosinic.polyribocytidylic acid. Journal of General Virology, 71, pp. 3061–3066.

ABOAGYE-MATHIESEN, G., TOTH, F. D., JUHL, C., NORSKOV-LAURITSEN, N., PETERSEN, P. M. and EBBESEN, P. (1991). Purification of human placental trophoblast interferon by two-dimensional high performance liquid chromatography. Preparative Biochemistry, 21, pp. 35–51.

ADOLF, G. A. (1987). Antigenic structure of human interferon ω1 (interferon $α_{11}$): Comparison with other human interferons. Journal of Virology 68, pp. 1669–1676.

ATHANASSAKIS, I., BLEACKLEY, R. C., PAETKAV, V., GUILBERT, L., BARR, P. J. and WEGMANN, T. G. (1987) The immunostimulating effect of a T cell and T cell lymphokines and on murine fetally derived placental cells. Journal of Immunology, 138, pp. 37–44.

BAGLIONI, C. (1979). Interferon-induced enzymatic activities and their role in the antiviral state. Cell, 17, pp. 255–264.

BERKOWITZ, R. S., HILL, J. A., KURTZ, C. C., and ANDERSON, D. J. (1988). Effects of activated leukocytes (lymphokines and monokines) on the growth of malignant trophoblast cells in vitro. American Journal of Obstetrics and Gyenacology, 158, pp. 199–203.

BOCCI, V., PAULESU, L. and RICCI, M. G. (1985). The physiological interferon production: IV. Production of interferon by the perfused human placenta at term. Proceedings of the Society of Experimental Biology and Medicine, 180, pp. 137–143.

BRADFORD, M. M. (1976). A rapid and sensitive method for the quantitation of microgram quantities of protein utilizing the principle of protein-dye binding. Analytical Biochemistry, 72, pp. 248–254.

BULMER, J. N., MORRISON, L. & JOHNSON, P. M. (1988). Expression of the proliferation markers Ki67 and transferrin receptor by human trophoblast population. Journal of Reproductive Immunology, 14, pp. 291–301.

BURKE, D. C., GRAHAM, C. F. & LEHMAN, J. H. (1978). Appearance of interferon inducibility and sensitivity during differentiation of murine teratocarcinoma cells in vitro. Cell, 13, pp. 243–248.

CAPON, D. J., SHERPARD, H. M. and GOEDDEL, D. V. (1985). Two distinct families of human and bovine interferon genes are coordinately expressed and encode functional polypeptides. Molecular and Cellular Biology, 5, pp. 768–779.

CHARD, T., CRAIG, P. H., MENABAWEY, M. and LEE, C. (1986). Alpha interferon in human pregnancy. British Journal of Obstetrics and Gynaecology, 93, pp. 1145–1149.

CHIN, T. W., ANK, B. J., STROM, S. R. and STIEHM, E. R. (1986). Enhanced interferon production and lymphokine-activated cytotoxicity of human placenta cells. Cellular Immunology, 113, pp. 1–9.

CORRETTINI, J. C., BRUNNER, K. T., LINDAHL, P. & GRESSER, I. (1973). Inhibitory effect of interferon preparations and inducers on multiplication of transplanted allogenic spleen cells and syngeneic bone marrow cells. Nature. London, 242, pp. 152–153.

CROSS, J. C. & ROBERTS, R. M. (1989). Porcine conceptuses secrete an interferon during the preattachment period of early pregnancy. Biology of Reproduction, 40, pp. 1109–1118.

DIANZANI, F., DOLEI, A., and DI MARCO, P. (1986). A new type of human interferon produced by peripheral blood mononuclear cells treated by inhibitors of transcription. Journal of Interferon Research, 6, pp. 43–50.

DOUGLAS, G. C. and KING, B. F. (1989). Isolation of pure villous cytotrophoblast from term human placenta using immunomagnetic microspheres. Journal of Immunological Methods, 119, pp. 259–268.

DOUGLAS, G. C. and KING, B. F. (1990). Differentiation of human trophoblast cells in vitro as revealed by immunocytochemical staining of desmoplakin and nuclei. Journal of Cell sciences, 96, 131–141.

DUC-GOIRAN, P., ROBERT-GALLIOT, B., LOPEZ, J. and CHANY, C. (1985). Unusually apparently constitutive interferons and antagonists in human placental blood. Proceedings of the National Academy of Sciences USA, 82, pp. 5010–5014.

FISHER, P. B. & GRANT, S. (1985). Effects of interferons on differentiation of normal and tumor cells. Pharmacology and Therapeutics, 27, pp. 143–166.

FISHER, S. J., CUI, T. -Y., ZHANG, L., HARTMAN, L., GRAHL, K., GUO-YANG, Z., TARPEY, J. AND DAMSKY, C. H. (1989) Adhesive and degradative properties of human placental cytotrophoblast cells in vivo. Journal of Cell Biology, 109, pp. 891–902.

HAUPTMANN, R. & SWETLY, P. (1985). A novel class of human type 1 interferons. Nucleic Acids Research, 13, pp. 4739–4749.

HIRSCH, M. S., ELLIS, D. A., PROFFITT, M. R. & BLACK, P. H, (1974). Immunosuppressive effects an interferon preparation in vivo. Transplantation, 17, pp. 234–236.

HOWATSON, A. G., FARQUHARSON, M., MEAGER., A., McNICOL, A. M., AND FOULIS, A. K. (1988). Localization of α-interferon in the human feto-placental unit. Journal of Endocrinology, 119, pp. 531–534.

KLEIN, J. O., REMINGTON, J. S. & MARCY, S. M. (1976). An introduction to infection of the and newborn infants. In Infectious Disease of the Foetus and Newborn, pp. 1–32. Edited by J. S. Remington & J.O. Klein. Philadelphia: W. B. Saunders.

LAEMMLI, U. K. (1970). Cleavage of structural proteins during the assembly of the head of bacteriophage T4. Nature, 227, pp. 680–685.

LEBON, P., GIRARD,. S., THEPOT, F. AND CHANY, C. (1982). The presence of interferon in human amniotic fluid. Journal of General virology, 59, 393–396.

LOWRY., O. H., ROSEBROUGH, N.J., FARR, A. L., and RANDALL, R. L., (1951) Protein Measurement with the Folin Phenol Reagent. J. Biol. Chem. 193, 265–275

MARIE, I., SVAB, J., NADINE, R., GALABRU, J., and HOVANESSIAN, A. G. (1990). Differential expression and distinct structure of 69- and 100-kDa forms of 2-5A synthetase in human cells treated with interferon. Journal of Biological Chemistry, 265, pp. 18601–18607.

MOBRAATEN, L. E., DE MAEYER, E. & MAEYER-GUIGNARD, J. (1973). Prolongation of allograft survival in mice by inducers of interferon. Transplantation, 16, pp. 415–420.

MOSMANN T. (1983). Rapid colorimetric assay for cellular growth and survival application to proliferation and cytotoxicity assays. J. Immunol. Methods 65, pp. 55–63.

REMINGTON, J. S. & DESMONTS, G. (1976). Toxoplasmosis. In Infectious Disease of the Foetus and Newborn, pp. 191–332. Edited by J. S. Remington & J. O. Klein. Philadelphia: W. B. Saunders.

ROSENBLUM, M. K., YUNG, W. K. A., KELLEHER, P. J., RUZICKA, F., STECK, P. A. and BORDEN, E. C. (1990). Growth inhibitory effects of interferon-β but not interferon-α on human glioma cells; correlation of receptor binding, 2', 5'-oligoadenylate synthetase and protein kinase activity. Journal of Interferon Research, 10, pp. 141–151.

SEKIYA, S,, KUWATA, T., ISHIGE, H., TOMITA, Y. and TAKAMIZAWA, H. (1986). Effects of human interferons on human choriocarcinoma cells in vitro and in vivo. Gynecol. Oncol. 25, pp. 115–124.

TOTH, F. D., JUHL, C., NORSKOV-LAURITSEN N., PETERSEN, P. M. and EBBESEN, P. (1990). Interferon production by cultured human trophoblast induced with double stranded polyribonucleotide. Journal of Reproductive Immunology, 17, pp. 217–227.

WILKINSON, M., and MORRIS, A. (1983). Interferon with novel characteristics produced by human mononuolear leukocytes. Biochemical Biophysics Research Communication, 111, pp. 489–503.

YAMAUCHI, T., WILSON, C, & ST. GEME, J. W., JR (1974) Transmission of live, attenuated mumps virus to the human placenta. New England Journal of Medicine, 290, pp. 710–712.

ZULLO. J. N., COCHRAN, D. H., HUANG, A. S. & STILES, C. D. (1985). Platelet-derived growth factors and double-stranded ribonucleic acids stimulate expression of the gene in 3T3 cells. Cell, 43, pp. 793–800.

We claim:

1. An isolated β-interferon protein which is identical or substantially identical to a human β-interferon protein produced by a human trophoblast cell said β-interferon protein being produced by a term trophoblast cell or a trophoblast cell derived from a provoked vaginal delivery, which trophoblast cell is a villous trophoblast which is not bound by magnetic beads carrying immobilized antibodies to the tissue types MHC-1, A, B, or C, the β-interferon being obtainable in purified form from a filtered (0.22 μm filter) supernatant of a stimulated culture of the trophoblast cells, by a purification scheme comprising either 1) High-performance dye-ligand affinity chromatography followed by applying the thus obtained interferon-containing fractions to High-performance immunoaffinity chromatography using immobilized anti-β-interferon antibodies or 2) High-performance dye-ligand chromatography followed by Reversed phase HPLC, the β-interferon possessing at least one of the following characteristics i–iv:

i) the β-interferon in purified form appears substantially as only one silver-stainable band showing antiviral activity with a molecular weight in the range of 22–26 kDa, in a slab SDS-PAGE, applying an amount of β-interferon of 40.000 IU, under reducing conditions using 5% 2-mercaptoethanol or under non-reducing conditions without using 2-mercaptoethanol, ii) the antiviral activity of the β-interferon, as measured by inhibition of vesicular stomatitis virus plaque formation in a human amniotic cell line WISH cells (ATCC, CCL 25), is retained in a pattern which resembles the specific pattern of retainment to an extent of about 55% of the initial value of antiviral activity after 3 hours at a temperature of 37° C., and to an extent of about 45–55%, in particular about 48–52%, after 10 minutes at a temperature of 56° C., 38–47%, in particular about 41–45%, after 15 minutes at a temperature of 56° C., 0–10%, in particular about 1–5%, after 60 minutes at a temperature of 56° C., iii) the β-interferon substantially retains its antiviral activity after storage in 0.1M glycine at pH 2 for 24 or even 48 hours, as measured by inhibition of the plaque formation in human amniotic cell line WISH caused by vesicular stomatitis virus (VSV), Indiana strain, iv) the β-interferon shows a high degree of hydrophobicity as indicated by its requiring a concentration of 50% of the hydrophobic eluent ethylene glycol in 0.02M sodium phosphate buffer pH 7.2 containing 1.0M NaCl to be eluted from the High performance dye-ligand affinity chromatography column.

2. A β-interferon protein according to claim 1, which is a glycoprotein.

3. A β-interferon according to claim 1 which in purified form appears substantially as only one silver-stainable band showing antiviral activity with a molecular weight in the range of 23–25 kDa, determined as described in claim 1.

4. A β-interferon according to claim 1 which in purified form appears substantially as only one silver-stainable band showing antiviral activity with a molecular weight of 24 kDa, determined as described in claim 1a).

5. An β-interferon protein according to claim 1, which has antiproliferal effect, as determinable by standard methods.

6. A β-interferon protein according to claim 1, which is capable of protecting human cell lines WISH (ATCC), GM 2504 and GM 2767 trisomy 21 fibroblasts (Cell Repository, Cambden, N.J., U.S.A.) against an infection with vesicular stomatitis virus (VSV), Indiana strain, but is not capable of protecting bovine cell line MBDK against a vesicular stomatitis virus (VSV), Indiana strain, infection.

7. A β-interferon protein according to claim 1, which is in substantially pure form.

8. A β-interferon protein according to claim 1, which has a purity of at least 95%, as measured by densiometric scanning of a Comassie Blue gel at 595 nm.

9. A β-interferon protein according to claim 1, which has a purity of at least 99%, as measured by densiometric scanning of a Comassie Blue gel at 595 nm.

10. A β-interferon protein according to claim 1, which, when having been subjected to high performance dye-ligand affinity chromatography, has a purity of at least 95%, as measured by densiometric scanning of a Comassie Blue gel at 595 nm.

11. A β-interferon protein according to claim 1, which, when having been subjected to high performance dye-ligand chromatography and subsequent high performance immunoaffinity chromatography using immobilized anti-$α_I$-interferon antibodies, has a purity of at least 99%, as measured by densiometric scanning of a Coomassie Blue gel at 595 nm.

12. A β-interferon protein according to claim 1, which has a specific activity of at least about $1.0 \times 10^8$ IU/mg of protein.

13. A pharmaceutical composition comprising an interferon according to claim 1 in association with a stabilizer.

14. A composition according to claim 13 in which the stabilizer is human albumin.

15. An isolated human β-interferon protein, purified to a specific activity of at least about $1.03 \times 10^8$ IU/mg., which is obtainable from human trophoblast cells but not from human fibroblast cells, and which retains 55% of its antiviral activity at 37° C. for three hours.

16. The isolated protein of claim 15, further characterized as having an apparent molecular weight in the range of 22–26 kDA when determined by sodium dodecylsulfate-polyacrylamide gel electrophoresis (SDS-PAGE).

17. The isolated protein of claim 15, further characterized as having a heat resistant antiviral activity, said antiviral activity, as measured by inhibition of vesicular stomatititis virus plaque formation in human amniotic WISH cells which is retained to the extent of about 45–55% of initial activity after 10 minutes at 56° C., 28–47% after 15 minutes at 56° C., and 0–10% after 60 minutes at 56° C.

* * * * *